(12) United States Patent
Diebold et al.

(10) Patent No.: US 10,617,363 B2
(45) Date of Patent: Apr. 14, 2020

(54) METHODS AND SYSTEMS FOR ANALYZING GLUCOSE DATA MEASURED FROM A PERSON HAVING DIABETES

(71) Applicant: Roche Diabetes Care, Inc., Indianapolis, IN (US)

(72) Inventors: Eric R Diebold, Fishers, IN (US); Alan Greenburg, Indianapolis, IN (US); David L Duke, Fishers, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 718 days.

(21) Appl. No.: 14/677,148

(22) Filed: Apr. 2, 2015

(65) Prior Publication Data
US 2016/0287184 A1 Oct. 6, 2016

(51) Int. Cl.
*A61B 5/00* (2006.01)
*A61B 5/145* (2006.01)

(52) U.S. Cl.
CPC .......... *A61B 5/7275* (2013.01); *A61B 5/0022* (2013.01); *A61B 5/14532* (2013.01);
(Continued)

(58) Field of Classification Search
CPC . A61B 5/14532; A61B 5/4839; A61B 5/7275; A61B 5/746
See application file for complete search history.

(56) References Cited

U.S. PATENT DOCUMENTS 7,291,107 B2 11/2007 Hellwig et al.
8,579,854 B2 11/2013 Budiman et al.
(Continued)

FOREIGN PATENT DOCUMENTS

EP 2762073 A1 8/2014
WO 2013/032965 A1 3/2013
(Continued)

OTHER PUBLICATIONS

International Search Report pertaining to Appln. No. PCT/US2017/019025, filed Feb. 23, 2017, 5 pages.
(Continued)

*Primary Examiner* — Etsub D Berhanu
*Assistant Examiner* — Michael A Catina
(74) *Attorney, Agent, or Firm* — Dinsmore & Shohl, LLP

(57) ABSTRACT

Methods and systems are disclosed analyzing a glucose level of a person having diabetes. The method, in at least one example, comprises receiving into a computing device a plurality of measured glucose values from a continuous glucose monitoring system coupled to a person having diabetes, analyzing the plurality of measured glucose values with a probability analysis tool on the computing device to determine a glucose threshold ($g_{I_0}$), and a boundary glucose value ($g_p$) at a probability threshold where the person having diabetes requires at least a predetermined insulin dose, and comparing, with the computing device, the boundary glucose value ($g_p$) to the glucose threshold ($g_{I_0}$), wherein if the boundary glucose value ($g_p$) is greater than the glucose threshold ($g_{I_0}$) then the computing device performs an alert on a user interface.

28 Claims, 19 Drawing Sheets

(52) U.S. Cl.
CPC .......... *A61B 5/4839* (2013.01); *A61B 5/7225* (2013.01); *A61B 5/7246* (2013.01); *A61B 5/7282* (2013.01); *A61B 5/742* (2013.01); *A61B 5/7405* (2013.01); *A61B 5/746* (2013.01); *A61B 5/7455* (2013.01); *A61B 5/7475* (2013.01)

(56) References Cited

U.S. PATENT DOCUMENTS

| | | | |
|---|---|---|---|
| 8,579,879 | B2 | 11/2013 | Palerm et al. |
| 8,734,422 | B2 | 5/2014 | Hayter |
| 2004/0167464 | A1* | 8/2004 | Ireland .............. A61M 5/14244 604/66 |
| 2006/0047192 | A1 | 3/2006 | Hellwig et al. |
| 2009/0105572 | A1 | 4/2009 | Malecha |
| 2010/0262434 | A1 | 10/2010 | Shaya |
| 2011/0071464 | A1 | 3/2011 | Palerm |
| 2011/0184267 | A1 | 7/2011 | Duke et al. |
| 2011/0257627 | A1 | 10/2011 | Hovorka |
| 2011/0313674 | A1 | 12/2011 | Duke et al. |
| 2012/0165638 | A1 | 6/2012 | Duke et al. |
| 2012/0166126 | A1 | 6/2012 | Engelhardt et al. |
| 2014/0005505 | A1 | 1/2014 | Peyser et al. |
| 2014/0066884 | A1 | 3/2014 | Keenan et al. |
| 2014/0066887 | A1* | 3/2014 | Mastrototaro ...... A61M 5/1723 604/504 |
| 2014/0083867 | A1 | 3/2014 | Schaible |
| 2014/0088392 | A1 | 3/2014 | Bernstein et al. |
| 2014/0100435 | A1 | 4/2014 | Duke et al. |
| 2014/0118138 | A1 | 5/2014 | Cobelli et al. |
| 2014/0235981 | A1* | 8/2014 | Hayter ................ A61M 5/1723 600/347 |
| 2015/0273147 | A1 | 10/2015 | Duke et al. |

FOREIGN PATENT DOCUMENTS

| | | |
|---|---|---|
| WO | 2015/183689 A1 | 3/2015 |
| WO | 2015073211 A1 | 5/2015 |

OTHER PUBLICATIONS

Written Opinion pertaining to Appln. No. PCT/US2017/019025, filed Feb. 23, 2017, 8 pages.
International Search Report pertaining to Appln. No. PCT/US2017/019013, filed Feb. 23, 2017, 5 pages.
Written Opinion pertaining to Appln. No. PCT/US2017/019013, filed Feb. 23, 2017, 8 pages.
International Search Report pertaining to Appln. No. PCT/US2017/019030, filed Feb. 23, 2017, 5 pages.
Written Opinion pertaining to Appln. No. PCT/US2017/019030, filed Feb. 23, 2017, 9 pages.
International Search Report and Written Opinion completed Jun. 10, 2016, pertaining to PCT/US2016/025502 filed Apr. 1, 2016.
Schwartz et al., "Use of Automated Bolus Calculators for Diabetes Management," Diabetes Management, Touch Medical Media 2013, 92-95.
International Search Report dated Aug. 21, 2017, pertaining to PCT/US2017/029072, filed Apr. 24, 2017, 6 pages.
Written Opinion dated Aug. 21, 2017, pertaining to PCT/US2017/029072, filed Apr. 24, 2017, 14 pages.
Jaramillo et al., Prediction of Postprandial Blood Glucose Under Intra-Patient Variability and Uncertainty and Its Use in the Design of Insulin Disposing Strategies for Type I Diabetic Patients, Jul. 22, 2011, pp. 1-178, URL:http://dugi-doc.udg.edu/bitstream/handle.
International Search Report pertaining to PCT application No. PCT/US2017/031661, filed May 9, 2017, 6 pages.
Written Opinion pertaining to PCT application No. PCT/US2017/031661, filed May 9, 2017, 11 pages.
Kovatchev, B.P., et al., Symmetrization of the Blood Glucose Measurement Scale and Its Applications, Diabetes American Diabetes Association, vol. 20., No. 11, Nov. 1, 1997, pp. 1655-1658, USA.
International Search Report pertaining to PCT application No. PCT/US2017/031662, filed May 9, 2017, 6 pages.
Written Opinion pertaining to PCT application No. PCT/US2017/031662, filed May 9, 2017, 9 pages.
Hughes, et al., Hypoglycemia Prevention via Pump Attenuation and Red-Yellow-Green "Traffic" Lights Using Continuous Glucose Monitoring and Insulin Pump Data, Journal of Diabetes Science and Technology, vol. 4, No. 5, Sep. 1, 2010, pp. 1146-1155, USA.
U.S. Non-Final Office Action dated May 31, 2018 pertaining to U.S. Appl. No. 15/170,468, 12 pages.

\* cited by examiner

METHODS AND SYSTEMS FOR ANALYZING GLUCOSE DATA MEASURED FROM A PERSON HAVING DIABETES

TECHNICAL FIELD

The present disclosure generally relates to processing glucose data measured from a person having diabetes and, in particular, for sending an alert to the person if the probability of needing insulin exceeds a threshold level.

BACKGROUND

As background, people suffer from either Type I or Type II diabetes in which the sugar level in the blood is not properly regulated by the body. Many of these people may use continuous glucose monitoring (CGM) to monitor their glucose level on an ongoing basis. In order to perform CGM, a glucose sensor may be placed under the skin which is capable of measuring the glucose level of the person in the interstitial fluid. The glucose sensor may periodically measure the glucose level of the person at a known time interval, such as every one minute, and transmit the results of the glucose measurement result to an insulin pump, blood glucose meter, smart phone or other electronic monitor.

SUMMARY

In at least one embodiment of the present disclosure, a method and system for analyzing a glucose level of a person having diabetes is described.

In at least one embodiment of the method for analyzing a glucose level of a person having diabetes, the method comprises:
receiving into a computing device a plurality of measured glucose values from a continuous glucose monitoring system coupled to a person having diabetes;
analyzing the plurality of measured glucose values with a probability analysis tool on the computing device to determine a glucose threshold ($g_{I_0}$), and a boundary glucose value ($g_\rho$) at a probability threshold where the person having diabetes requires at least a predetermined insulin dose; and
comparing, with the computing device, the boundary glucose value ($g_\rho$) to the glucose threshold ($g_{I_0}$), wherein if the boundary glucose value ($g_\rho$) is greater than the glucose threshold ($g_{I_0}$) then the computing device performs an alert on a user interface.

In at least one embodiment of the present disclosure, A system for analyzing a glucose level of a person having diabetes is disclosed. The system comprises:
a controller comprising a computer readable medium having computer executable instructions for performing the method comprising:
receiving into a computing device a plurality of measured glucose values from a glucose sensor coupled to a person having diabetes;
analyzing the plurality of measured glucose values with a probability analysis tool on the computing device to determine a probability (PID) that the person having diabetes requires at least a predetermined insulin dose; and
comparing, with the computing device, the probability (PID) to a threshold probability (PT), wherein if the probability (PID) is greater than the threshold probability (PT) then the computing device executes an alert;

a bolus calculator in communication with the controller, the bolus calculator capable of determining an insulin bolus based on the plurality of measured glucose values.

In at least one embodiment of the present disclosure, the method further comprises determining a maximum safe insulin bolus. Optionally, the method may also include producing an alarm on the user interface if a manual bolus request exceeds the maximum safe insulin bolus.

In at least one embodiment of the present disclosure, the boundary glucose value ($g_\rho$) is determined by the equation $$g_\rho = \sqrt{2\sigma_g^2} \, erf^{-1}(2\rho-1)+g,$$

wherein $\sigma_g^2$ is a variance of glucose measurement, $\rho$ is the probability threshold that the person having diabetes requires at least a predetermined insulin dose, and g is a glucose result from the plurality of measured glucose values, In at least one embodiment of the present disclosure, the glucose threshold ($g_{I_0}$) is determined by the equation $$g_{I_0} = g_m + cI_0,$$

wherein, $g_m$ is a maximum allowable glucose, c is a correction factor, and $I_0$ is a minimum insulin dose.

In at least one embodiment of the present disclosure, the predetermined insulin dose is 1 unit.

In at least one embodiment of the present disclosure, the glucose threshold is dependent on the time of day. Additionally, in at least one embodiment, a day is broken into a plurality of time blocks, at least one of the plurality of time blocks having a different glucose threshold than the remaining time blocks.

In at least one embodiment of the present disclosure, the probability threshold is selected from a group consisting of 99%, 98%, 90%, 75%, and 50%.

In at least one embodiment of the present disclosure, the predetermined insulin dose is higher during a period of sleep than a waking period.

In at least one embodiment of the present disclosure, the plurality of measured glucose values comprises periodic glucose measurements taken approximately every one minute.

In at least one embodiment of the present disclosure, at least one of the maximum allowable glucose, the minimum insulin dose, and the correction factor are supplied by a bolus calculator.

In at least one embodiment of the present disclosure, the alert may be a display, sound, vibration, or any combination thereof. Optionally, the alert may also indicate that a glucose measurement should be taken.

In at least one embodiment of the present disclosure, the alert and/or the alarm generated may be temporarily turned off for a period of time following a meal, a correction bolus or a BG measurement. In at least one embodiment, the period of time may be the length of offset time as defined by the bolus calculator, such as 15 min, 30 min, 45 min, 1 hour, or 2 hours.

In at least one embodiment of the present disclosure, the method may further comprise administering a predetermined safety insulin bolus to the person having diabetes, if the glucose measurement is not performed and a correction dose is not administered. Optionally, the glucose measurement may be a self-monitored blood glucose measurement or an additional measurement taken by the continuous glucose monitoring system and triggered by the user.

In at least one embodiment of the present disclosure, the method may further comprise determining an insulin bolus dose with the computing device using the glucose measurement.

In at least one embodiment of the present disclosure, the determining of the insulin bolus dose uses at least one of a rate of change measurement of the plurality of measured glucose values, a trend in the plurality of measured glucose values, and a pattern in the plurality of measured glucose values.

In at least one embodiment of the present disclosure, the determining of the insulin bolus dose uses at least one rate of change measurement of the plurality of measured glucose values, and a predicted glucose value, wherein the correction dose is $$I_c = \frac{1}{c}(g + \dot{g}\tau - g_t);$$

wherein
c is a correction factor,
g is a glucose result from the plurality of measured glucose values,
$\dot{g}$ is a glucose rate-of-change,
$\tau$ is a predicted time, and
$g_t$ is a predicted glucose level at time t.

In at least one embodiment of the present disclosure, time t is about 20 minutes to about 60 minutes.

In at least one embodiment of the present disclosure, the method performed on the controller further comprises determining a maximum safe insulin bolus.

In at least one embodiment of the present disclosure, controller is configured to produce an alarm on the user interface if a manual bolus request entered in the user interface exceeds the maximum safe insulin bolus.

In at least one embodiment of the present disclosure, the method performed by the computer executable instructions further comprises determining a glucose rate of change of the plurality of measured glucose values, the glucose rate of change being used by the bolus calculator to modify the insulin bolus.

In at least one embodiment of the present disclosure, the controller further comprising a user interface, wherein the method further comprises displaying on the user interface the modified insulin bolus.

In at least one embodiment of the present disclosure, the rate of change may be used to predict a glucose level at a future time for use by the bolus calculator.

BRIEF DESCRIPTION OF THE DRAWINGS

The embodiments set forth in the drawings are illustrative and exemplary in nature and not intended to limit the inventions defined by the claims. The following detailed description of the illustrative embodiments can be understood when read in conjunction with the following drawings, where like structure is indicated with like reference numerals and in which:

DETAILED DESCRIPTION

The embodiments described herein generally relate to methods and systems for processing glucose data measured from a person having diabetes and, in particular, for alerting the person with diabetes when the probability of their needing an insulin dose exceeds a defined threshold. For the purposes of the present disclosure, "measured glucose values" are the glucose levels of the person as measured by a glucose sensor; "actual glucose level" is the actual glucose level of the person; and "estimated glucose level" is the estimated glucose level of the person, which may be based on the measured glucose results.

Figure 1:
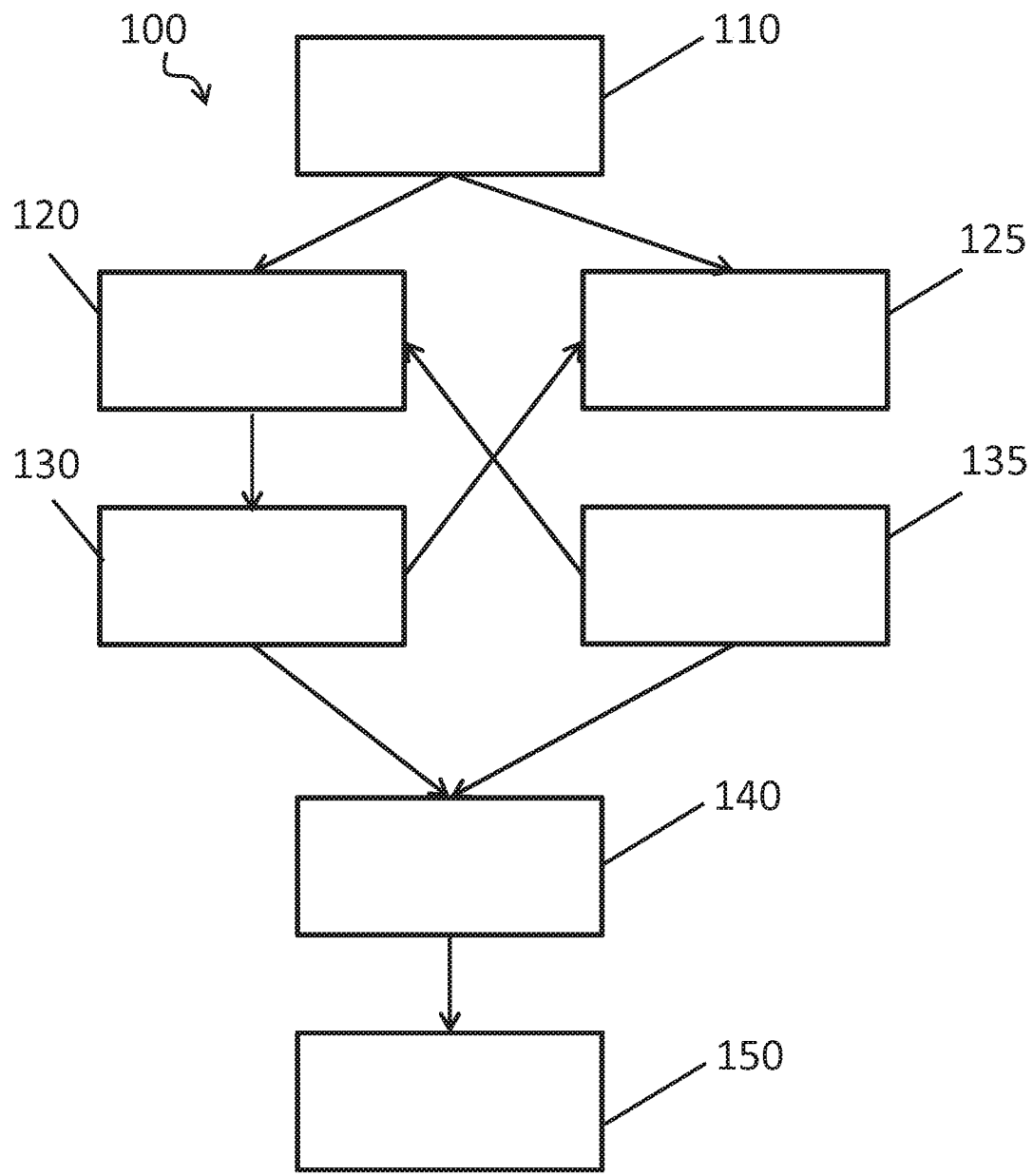
FIG. 1 depicts a flowchart showing a method of analyzing a glucose level of a person with diabetes, according to at least one embodiment of the present disclosure.

In FIG. 1, a method 100 for analyzing a glucose level of a person having diabetes, according to at least one embodiment, is disclosed. Exemplary method 100 comprises: receiving into a computing device a plurality of measured glucose values from a continuous glucose monitoring system coupled to a person having diabetes (exemplary receiving step 110), analyzing the plurality of measured glucose values with a probability analysis tool on the computing device to determine a glucose threshold ($g_{I_0}$), and a boundary glucose value ($g_p$) at a probability threshold where the person having diabetes requires at least a predetermined insulin dose (exemplary analyzing step 120), and comparing, with the computing device, the boundary glucose value ($g_p$) to the glucose threshold ($g_{I_0}$), wherein if the boundary glucose value ($g_p$) is greater than or equal to the glucose threshold ($g_{I_0}$) then the computing device performs an alert on a user interface (exemplary comparing step 130). In at least one embodiment of method 100, the computing device may optionally determine a maximum safe insulin bolus (exemplary step 125). If a manual bolus request is entered which would exceed the maximum safe bolus, an alarm is given (exemplary alarm step 135). In at least one embodiment of step 135, the alarm may comprise a notice to the person with diabetes and a plurality of options for responding to the notice.

The computing device of method 100, in at least one embodiment of the present disclosure, may comprise a blood glucose meter, an insulin pump, a microprocessor coupled to a continuous glucose monitoring system, a microcontroller, a cellular phone, a smart phone, a personal digital assistant, a personal computer, or a computer server. The computing device may also be referred to herein as a "glucose monitor" in some embodiments.

The continuous glucose monitoring system of method 100, in at least one embodiment, is physically coupled to the person having diabetes and configured to automatically measure the glucose level of the person. Glucose measurements from the continuous glucose monitoring system may occur at routine intervals, such as every minute, every 2 minutes, every 3 minutes, every 4 minutes, every 5 minutes, every 10 minutes, or every 15 minutes.

In exemplary receiving step 110, the computing device may be supplied with additional sources of data to use in the determination of the glucose threshold and/or the boundary glucose value in analyzing step 120. For example, the additional data may include maximum allowable glucose, a minimum insulin dose, and a correction factor may be used in the determination of the glucose threshold. At least some of the additional sources of data may be supplied by a bolus calculator.

The maximum allowable glucose, according to at least one embodiment, is that provided by a bolus calculator. This exemplary value is either the average of the upper and lower target that defines the glucose target range, or it is the upper boundary of the trapezoid that follows a significant disturbance such as a meal or correction insulin doses. A correction dose after a high BG measurement may correct to the maximum allowable glucose value. The correction dose may also be a dose beyond which further correction would not be recommended. In at least one embodiment, the bolus calculator also contains the insulin sensitivity factor or correction factor.

Further, in at least one embodiment, a recursive filter may supply the computing device with a state vector, which includes a glucose value, the glucose rate-of-change, and the glucose acceleration. Additionally, a recursive filter may supply the computing device with a covariance matrix in receiving step 110. The covariance matrix contains a measure of the accuracy of the state vector.

The glucose threshold ($g_{I_0}$) in at least one embodiment of analyzing step 120 may be computed using equation [1].

$$g_{I_0} = g_m + cI_0 \quad [1]$$

wherein,
$g_m$ is the maximum allowable glucose,
c is the correction factor, and
$I_0$ is the minimum insulin dose.

The minimum insulin dose may be specified in at least one embodiment to be a specific amount of insulin (such as 0.5, 1, 2, 3, 4 or 5 units), or as a percentage of the person with diabetes' total daily dose (such as 1%, 2%, 3%, 4%, 5%, 6%, 7%, 8%, 9%, or 10%).

The boundary glucose value ($g_p$) in at least one embodiment of analyzing step 120 may be computed using equation [2].

$$g_\rho = \sqrt{2\sigma_g^2}\, erf^{-1}(2\rho-1)+g \quad [2]$$

wherein
$\sigma_g^2$ is a variance of glucose measurement,
$\rho$ is the probability threshold that the person having diabetes requires at least a predetermined insulin dose, and
g is a glucose result from the plurality of measured glucose values, The probability threshold that the person having diabetes requires at least a predetermined insulin dose may, in at least one embodiment of the present disclosure, be 99%, 98%, 95%, 90%, 75% or 50%.

In at least one embodiment of the present disclosure, the predetermined insulin dose may be dependent on the time of day. For example, a day may be divided into a plurality of time blocks, where at least one of the plurality of time blocks has a different glucose threshold than at least one of the remaining time blocks. Moreover, the predetermined insulin dose may be higher during a period of sleep than a waking period. The predetermined insulin dose in at least one embodiment may be 0.5, 1, 2, 3, 4 or 5 units.

In at least one embodiment of comparing step 130, the alert may be a display, sound, vibration, any combination thereof, or any stimulus suitable to trigger the user to perform a task. Further, the alert may, in at least one embodiment, indicate that the user should take a glucose measurement. Such a glucose measurement may be a self-monitored blood glucose measurement, or an additional measurement taken by the continuous glucose monitoring system. The additional measurement by a continuous glucose monitoring system may be automatically conducted by the system, or initiated manually by the user.

Dosing of insulin may also be impacted by a situation called "insulin stacking," where an individual doses insulin without considering their remaining active insulin or current blood glucose level. At least one embodiment of the present disclosure provides a way for the CGM to be used to determine a maximum safe insulin bolus. If a manual bolus request is given for an amount greater than the maximum safe bolus, then the individual is notified and presented with a set of options. This discourages the practice of bolusing based on the CGM value and reduces the risk of insulin stacking.

In at least one embodiment of step 125, the algorithm used for the insulin stacking alarm is initiated by a manual bolus. Upon selection of the bolus amount, the controller receives a value for the maximum allowable glucose that is provided by the bolus calculator. This value is either the average of the upper and lower target that defines the glucose target range, or it is the upper boundary of the trapezoid that follows meals and correction insulin doses. A correction dose after a high BG measurement corrects to the maximum allowable glucose value. The bolus calculator also contains the insulin sensitivity factor or correction factor.

$g_m$ Max Allowable Glucose
c Correction factor or ISF (i.e. 30 mg/dl/UI)

The alarm in at least one embodiment of step 135 may be defined by two parameters. The first is the probability threshold that must be crossed in order to alarm. This is given by the probability that a measured value will be below the threshold. The second is maximum safe insulin dose. This is the threshold for alarming, and it is calculated based on the probability threshold.

$\rho_L$ Lower Probability threshold (i.e. 5%)
$\rho_U$ Upper probability threshold (i.e. 95%)
$g_L$ Glucose level for the lower probability threshold
$g_U$ Glucose level for the upper probability threshold
$I_S$ Maximum safe insulin dose
$I_U$ Upper or unsafe insulin dose. This is the dose that is more than the upper 95% of the glucose uncertainty range.

To determine if an alarm should be given the boundary for the lower $\rho$ quantile is calculated.

$$g_L = \sqrt{2\sigma_g^2} erf^{-1}(2\rho_L - 1) + g$$

$$g_U = \sqrt{2\sigma_g^2} erf^{-1}(2\rho_U - 1) + g$$

The maximum safe insulin dose is calculated from this lower percentile of the glucose uncertainty distribution.

$$I_S = \frac{g_L - g_m}{c}$$

If ($I > I_S$) then the manual bolus is greater than the maximum safe insulin dose. When this occurs the PwD is notified and given a set of options. These may include at least one of:
   Taking an SMBG and running the bolus calculator.
   Reducing the manual bolus to the maximum safe insulin dose.
   Canceling the bolus.
   Entering an amount of carbohydrates to associate with the dose.
   Tagging the bolus as pre-meal without entering the amount of carbohydrates.
   Over-riding the alarm and administering the bolus.

The unsafe safe insulin dose is calculated from the upper percentile of the glucose uncertainty distribution.

$$I_U = \frac{g_U - g_m}{c}$$

If ($I > I_U$) then the manual bolus is in the unsafe region for an insulin dose. When this occurs the PwD is notified and given a set of options. These may include at least one of:
   Taking an SMBG and running the bolus calculator.
   Reducing the manual bolus to the maximum safe insulin dose.
   Canceling the bolus.
   Entering an amount of carbohydrates to associate with the dose.
   Tagging the bolus as pre-meal without entering the amount of carbohydrates.

The method 100, in at least one embodiment, may additionally comprise the step of administering a safety insulin bolus to the person having diabetes if the blood glucose measurement is not performed and a correction dose is not administered (exemplary administering step 140). In an exemplary embodiment, the safety bolus may be determined by the computing device using the boundary glucose value.

The method 100, in at least one embodiment, may further comprise the step of determining an insulin bolus dose with the computing device using the blood glucose measurement (exemplary determining step 150). In at least one embodiment, the computing device may comprise an embodiment of an insulin bolus calculator as described herein. In at least one embodiment, the computing device may determine a pre-prandial insulin dose. The step of determining an insulin bolus dose 150 may use at least one of a rate of change measurement of the plurality of measured glucose values, a trend in the plurality of measured glucose values, and a pattern in the plurality of measured glucose values.

In an exemplary embodiment of the step 150 of determining of the insulin dose, the step may use at least one rate of change measurement of the plurality of measured glucose values, and a predicted glucose value, where the correction dose is calculated using equation [3].

$$I_c = \frac{1}{c}(g + \dot{g}\tau - g_t) \qquad [3]$$

Wherein
   c is the correction factor,
   g is a glucose result from the plurality of measured glucose values,
   $\dot{g}$ is the glucose rate-of-change,
   $\tau$ is the predicted time, and
   $g_t$ is the predicted glucose level at time t.

In at least one embodiment, time t as used in exemplary step 150 may be about 20, about 30, about 40, about 50, or about 60 minutes.

In at least one embodiment of step 150 of determining insulin dose, the step may use a risk surface. This embodiment serves to calculate an adjustment to the maximum allowed glucose. Step 150, in at least this embodiment, uses the risk surface to define the curve where the risk surface is zero. For the risk surface, a hypoglycemic risk indicates a negative risk surface and a hyperglycemic risk indicates a positive risk surface. The optimal glucose value ($g0_{opt}$) is determined where the rate of change is zero. For the current rate of change, determine the optimal glucose value ($g1_{opt}$). If $g1_{opt} \leq g0_{opt}$, then set the adjustment to the maximum allowed glucose to zero. If $g1_{opt} > g0_{opt}$, then add the difference ($g1_{opt} - g0_{opt}$) to the maximum allowed glucose. Afterwards use the adjusted maximum allowed glucose to calculate the glucose threshold.

In at least one embodiment of the present disclosure, a computer-readable medium having computer executable instructions for performing a method for analyzing a glucose level of a person is disclosed. The method for analyzing a glucose level of a person may be any embodiment of method 100 as disclosed herein.

Figure 2:
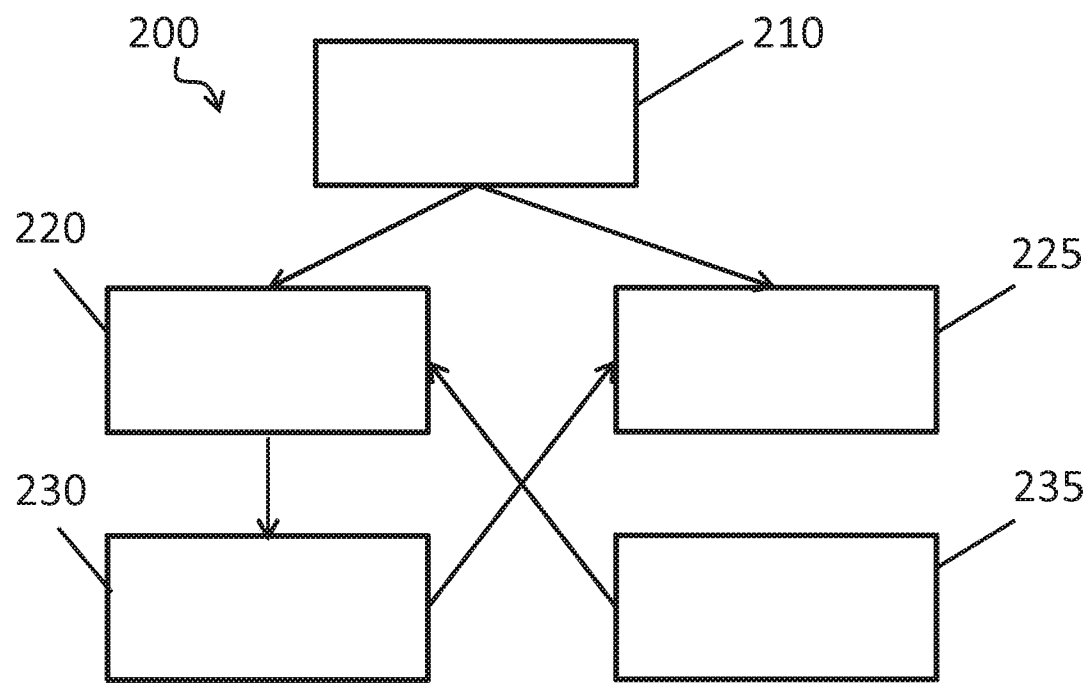
FIG. 2 depicts a flowchart showing a method of analyzing a glucose level of a person with diabetes, according to at least one embodiment of the present disclosure.

Turning to FIG. 2, an exemplary embodiment of method 200 that may be performed by computer executable instructions is shown. Exemplary method 200 comprises the steps of: receiving into a computing device a plurality of measured glucose values from a continuous glucose monitoring system coupled to a person having diabetes (exemplary receiving step 210), analyzing the plurality of measured glucose values with a probability analysis tool on the computing device to determine a boundary glucose value ($g_\rho$) at a probability threshold that the person having diabetes requires at least a predetermined insulin dose, and a glucose threshold ($g_{I_D}$) (exemplary analyzing step 220), comparing, with the computing device, the boundary glucose value ($g_\rho$) to the glucose threshold ($g_{I_D}$), wherein if the boundary glucose value ($g_\rho$) is greater than the glucose threshold ($g_{I_D}$) then the computing device executes an alert on a user interface (exemplary comparing step 230). In at least one embodiment of method 200, the computing device may optionally determine a maximum safe insulin bolus (exemplary step 225). If a manual bolus request is performed which would exceed the maximum safe bolus, an alarm is given (exemplary alarm step 235). In at least one embodiment of step 235, the alarm may comprise a notice to the person with diabetes and a plurality of options for responding to the notice.

In at least one embodiment of method 100 or 200, the alert generated in step 130/230 and/or the alarm generated in step 135/235 may be temporarily turned off for a period of time following a meal, a correction bolus or a BG measurement. In at least one embodiment, the period of time may be the length of offset time as defined by the bolus calculator, such as 15 min, 30 min, 45 min, 1 hour, or 2 hours.

Figure 3:
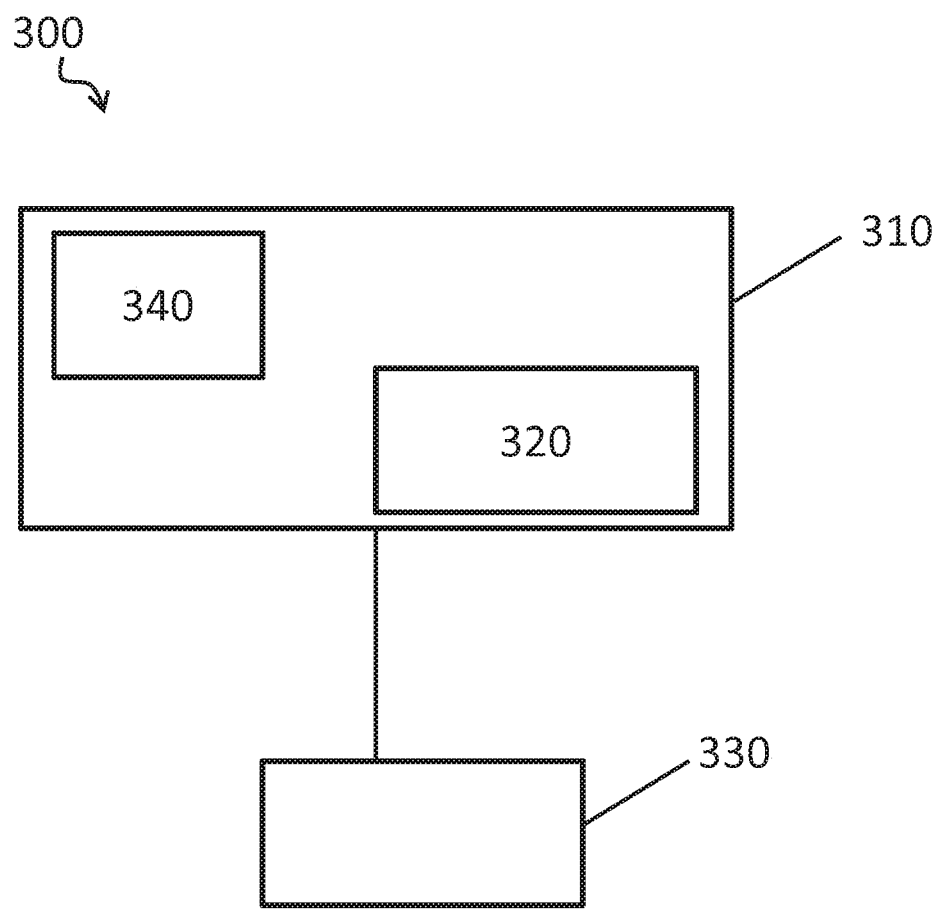
FIG. 3 depicts a system for analyzing a glucose level of a person having diabetes, according to at least one embodiment of the present disclosure.

In at least one embodiment of the present disclosure, a system 300 for analyzing a glucose level of a person having diabetes is shown in FIG. 3. The exemplary system 300 comprises: a controller 310 comprising a computer readable medium 320 having computer executable instructions for performing an embodiment of the present disclosure. In at least one embodiment, the method is dictated by computer executable instructions that include receiving into a computing device a plurality of measured glucose values from a glucose sensor coupled to a person having diabetes, analyzing the plurality of measured glucose values with a probability analysis tool on the computing device to determine a probability (PID) that the person having diabetes requires at least a predetermined insulin dose, and comparing, with the computing device, the probability (PID) to a threshold probability (PT), wherein if the probability (PID) is greater than the threshold probability (PT) then the computing device executes an alert.

Exemplary system 300 may further comprise a bolus calculator 330 that is in communication with the controller, where the bolus calculator is capable of determining an insulin bolus based on the plurality of measured glucose values.

The method performed by the computer executable instructions 320 in at least one embodiment of the present disclosure further comprises determining a glucose rate of change of the plurality of measured glucose values, where the glucose rate of change is used by the bolus calculator to modify the insulin bolus.

In at least one embodiment, the controller 310 further comprises a user interface 340 in communication with controller 310. The method executed by system 300 may also comprise the step of displaying on the user interface the modified insulin bolus. Additionally, a rate of change of the plurality of glucose results may be used to predict a glucose level at a future time for use by the bolus calculator.

Continuous Glucose Monitor

Figure 4:
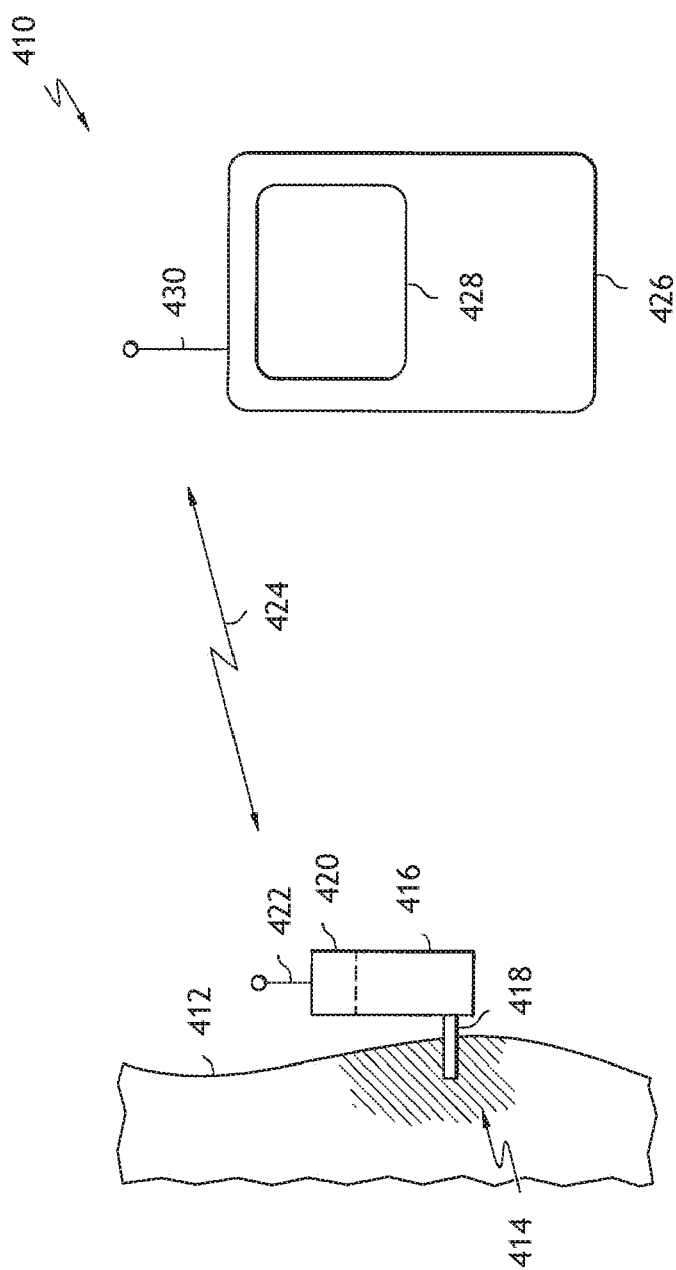
FIG. 4 depicts a continuous glucose monitoring (CGM) system according to at least one embodiment of the present disclosure.

FIG. 4 depicts an embodiment of a continuous glucose monitoring (CGM) system as used in at least one embodiment of the methods and systems described herein. Exemplary system 410 may comprise a glucose sensor 416 having a needle 418 which may be inserted under the skin 412 of the person having diabetes. The end of the needle 418 may be located in interstitial fluid 414, such that measurements taken by the glucose sensor 416 are based on the level of glucose in the interstitial fluid 414. The glucose sensor 416 may be placed on the abdomen of the person or other suitable location and may be secured with tape or adhesive (not shown). Furthermore, the glucose sensor 416 may be periodically calibrated in order to improve its accuracy. This periodic calibration may help correct for sensor drift due to sensor degradation and changes in the physiological condition of the sensor insertion site. The glucose sensor 416 may comprise other components as well, including but not limited to a wireless transmitter 420 and an antenna 422. Although depicted in FIG. 4 as a having a rectangular shape, it is contemplated that the glucose sensor 416 may assume other geometric shapes as well. Although the glucose sensor 416 may use a needle 418 to gain access to the person's blood, it may also use other suitable devices to access the person's blood or other fluid in order to take glucose measurements, including those yet to be discovered.

The glucose sensor 416, upon taking a measurement, may transmit the measured glucose value via a communication link 424 to a glucose monitor 426. The communication link 424 may be wireless, such as radio frequency, or "RF," in which the measured glucose values are transmitted via electromagnetic waves. For example, "Bluetooth®" is one type of wireless RF communication system which uses a frequency of approximately 2.4 Gigahertz (GHz). Another type of wireless communication scheme may use infrared light, such as the systems supported by the Infrared Data Association® (IrDA®). Other types of wireless communication are also contemplated, including present technologies and yet-to-be-developed technologies. The communication link 424 may be unidirectional (i.e., data may be transmitted only from the glucose sensor 416 to the glucose monitor 426), or it may be bidirectional (i.e., data may be transmitted between the glucose sensor 416 and the glucose monitor 426 in either direction). Furthermore, the communication link 424 may permit communication between two or more devices (e.g., a glucose sensor, a glucose monitor, an insulin pump, and so forth). Although FIG. 4 shows the communication link 424 as being wireless, it may alternatively be a wired link, such as for example Ethernet. Other public or proprietary wired or wireless links may be used as well.

Figure 5:
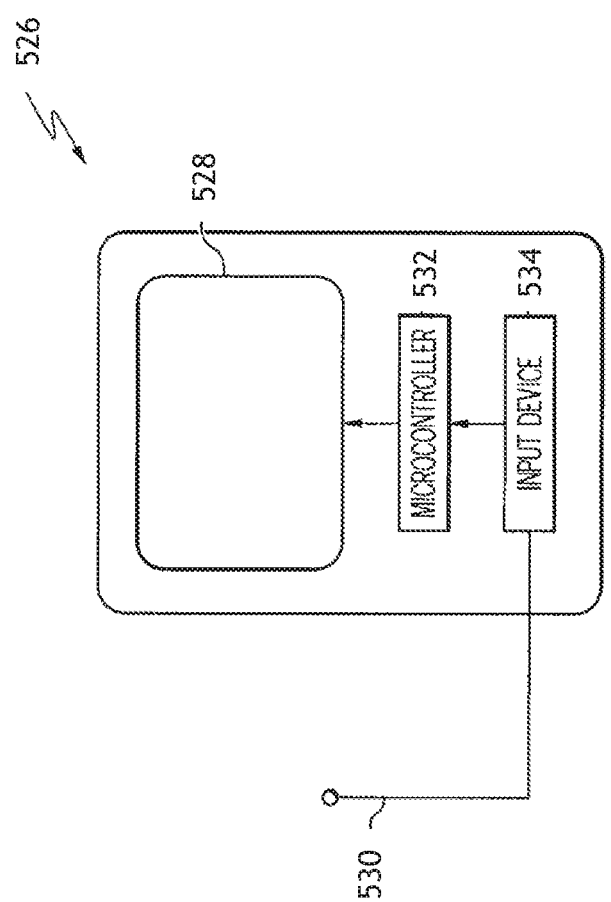
FIG. 5 depicts a glucose monitor according to at least one embodiment of the present disclosure.

FIG. 5 illustrates at least one embodiment of a glucose monitor 426, which may comprise a display 528, a microcontroller 532, and an input device 534. Examples of the glucose monitor 426 include, but are not limited to, a blood glucose meter, an insulin pump, a cellular phone, a smart phone, a personal digital assistant, a personal computer, or a computer server. The microcontroller 532 may be electrically coupled to the input device 534, which may be configured to receive a plurality of measured glucose values from a glucose sensor coupled to the person. The microcontroller 532 may be configured to receive the plurality of measured glucose values from the input device 534. The glucose monitor 426 may also be configured to store in memory (not shown) a plurality of measured glucose values received from the glucose sensor 416 over a period of time. The microcontroller 532 may be further configured to analyze the plurality of measured glucose values with a probability analysis tool configured to determine a probability of malfunction for the glucose sensor. Furthermore, the microcontroller 532 may be configured to estimate a glucose level of the person using a recursive filter configured to weight the plurality of measured glucose values with the probability of glucose sensor accuracy. Finally, the microcontroller 532 may be electrically coupled to the display 528 such that the microcontroller is configured to transmit to the display 528 information related to the estimated glucose level of the person. As discussed herein, the displayed information may include the estimated glucose level of the person and/or a predicted glucose level of the person at some time in the future. Furthermore, the display may also include an estimate of the quality or uncertainty of the estimated glucose level. Moreover, the displayed information may include warnings, alerts, etc. regarding whether the estimated or predicted glucose levels of the person is hypoglycemic or will become hypoglycemic at some time in the future. This may take place, for example, if the person's glucose level falls below (or is predicted to fall below) a predetermined hypoglycemic threshold, such as 50 milligrams of glucose per deciliter of blood (mg/dl). Further, the display 538 may further include an embodiment of an alert if the probability of the person needing a predefined dose of insulin falls above a defined threshold.

The microcontroller 532 may be an 8-bit device, a 16-bit device, or any other suitable device, and may have on-chip peripherals which facilitate its operation. For example, the microcontroller 532 may have internal memory for storing a computer program, internal memory for data storage, and internal memory for non-volatile storage of parameters used by the microcontroller during its operation. Furthermore, the microcontroller 532 may have timers, serial communication ports, interrupt controllers, and so forth. The microcontroller 532 may also be part of an application-specific integrated circuit (ASIC) that may include other circuitry which facilitates the operation of the glucose monitor 426. The input device 534 may be a wireless communication module configured to wirelessly receive measured glucose values from a glucose sensor (as shown in FIG. 4). As such, an antenna 530 may be used to improve the robustness of the wireless connection. Alternatively, the input device 534 may be a wired communication module that receives the measured glucose values through a wired connection, such as for example via Ethernet or similar protocol. The display 528 may comprise a liquid crystal display (LCD) or other suitable technology. The display 528 may also be configured to tactilely communicate information to the person, such as for example by vibrating.

Figure 6:
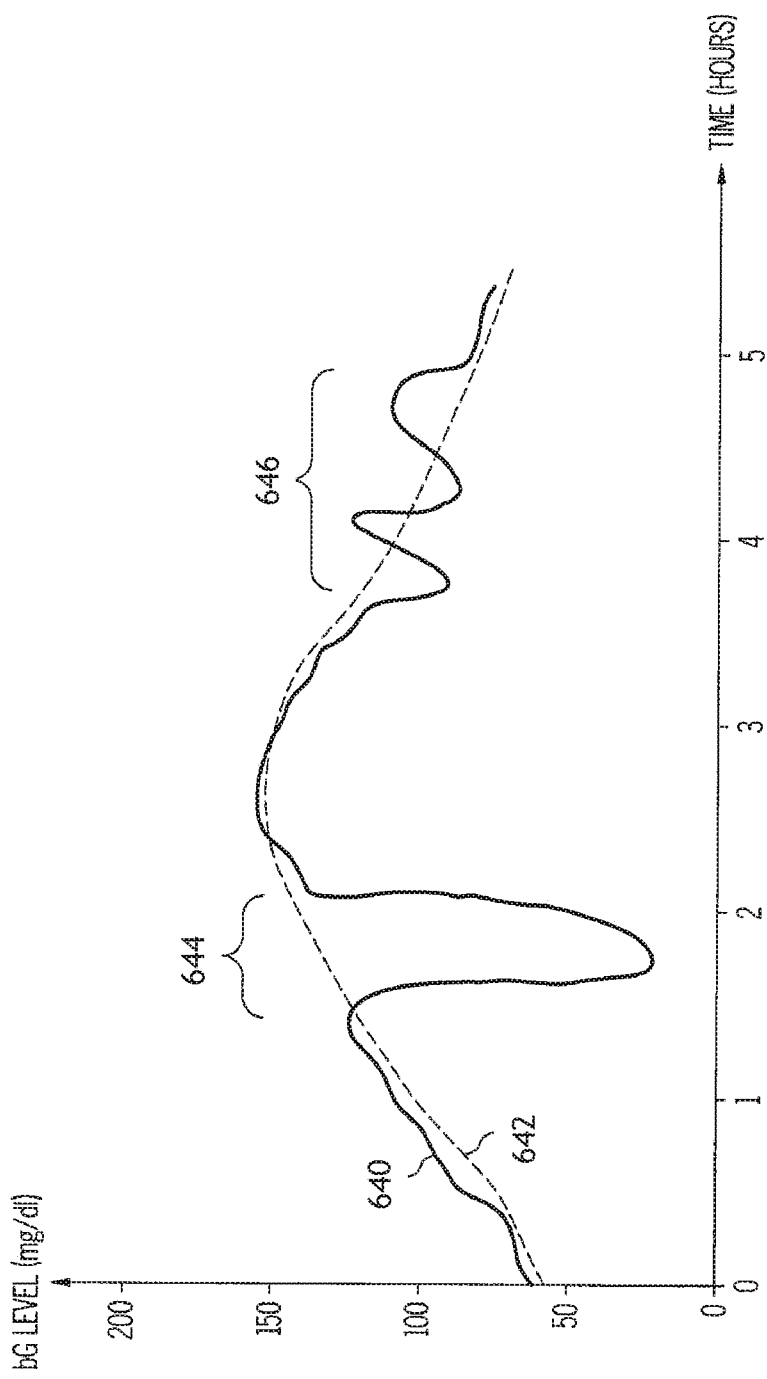
FIG. 6 depicts a graph of measured glucose values and actual glucose levels of the person according to at least one embodiment of the present disclosure.

FIG. 6 depicts an example of a two-dimensional graph of measured glucose values 640 from a glucose sensor coupled to a person having diabetes. The horizontal axis represents time in hours, while the vertical axis represents the measured and actual glucose level of the person in milligrams of glucose per deciliter of blood (mg/dl). Measurements may be automatically taken by the glucose sensor at a predetermined rate, such as every one minute. The measured glucose values 640 may generally correspond to the actual glucose level 642 of the person. However, the glucose sensor may malfunction from time to time, as shown during time period 644 in FIG. 6. The malfunction may be due to sensor dropout caused by physiological problems near the glucose sensor's needle, or it may be due to electrical problems with the glucose sensor itself. During the malfunction time period 644, the measured glucose values 640 may be substantially lower than the actual glucose level 642 of the person. At the conclusion of the malfunction time period 644, the measured glucose values 640 may recover such that they again correspond to the actual glucose level 642 of the person.

Referring still to FIG. 6, the glucose sensor may also exhibit noise from time to time, as shown during time period 646. The noise may be due to physical movement of the glucose sensor's needle relative to the skin or may be due to electrical noise inherent in the glucose sensor itself. During the noise time period 646, the measured glucose values 640 may vacillate, such that some results are above and some are below the actual glucose level 642. The noise may even appear to oscillate about the actual glucose level 642. At the conclusion of the noise time period 646, the measured glucose values 640 may recover such that they again closely correspond to the actual glucose level 642 of the person. Although shown as occurring at different times, malfunction and noise may occur at the same time as well as consecutively. Furthermore, the duration of the malfunction and/or noise may be shorter or longer than as depicted in FIG. 6.

Figure 7:
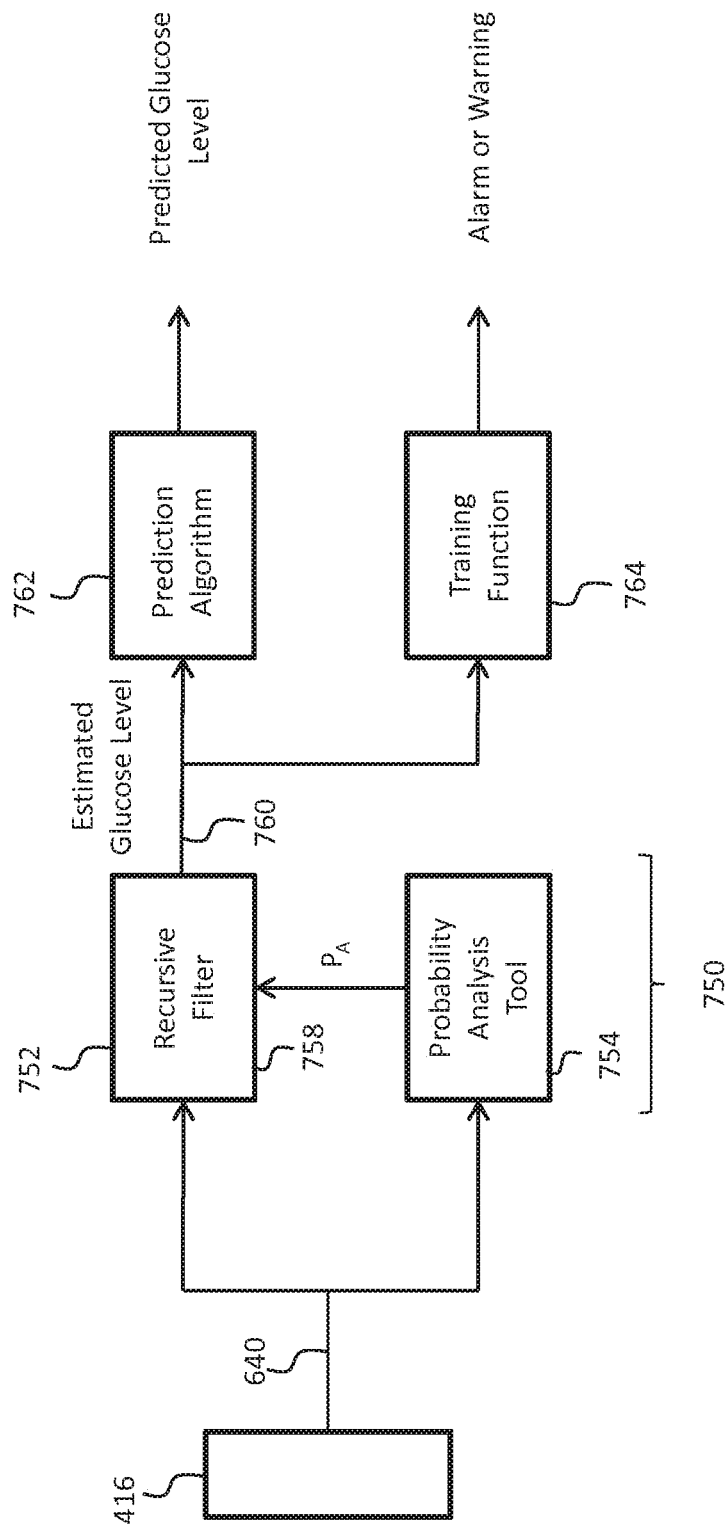
FIG. 7 depicts a probability analysis tool and a recursive filter according to at least one embodiment of the present disclosure.

It is against the above background that embodiments according to the present disclosure are provided which estimate the person's actual glucose level in the presence of sensor noise and/or sensor malfunction. FIG. 7 depicts a system 750 configured to estimate the glucose level of the person. The system 750 may receive the measured glucose values 640 from a glucose sensor 416 which may be coupled to a person having diabetes (not shown). The glucose sensor 416 may be coupled to the person as previously described herein or in any suitable fashion. The glucose sensor 416 may be configured to periodically measure the glucose level of the person, such as for example every one minute, and transmit the measured glucose values 640 to the system 750 (e.g., via a communication link as described hereinbefore).

The system 750 for estimating the glucose level of a person having diabetes may comprise a probability analysis tool 754 and a recursive filter 752. The probability analysis tool 754 may be configured to receive the measured glucose values 640 and calculate the probability of glucose sensor accuracy $P_A$ 758, i.e., the probability that that glucose sensor 416 is functioning normally (i.e., not malfunctioning). The probability of glucose sensor accuracy $P_A$ 758 may be based solely on observable data, such as the measured glucose values 640 and/or changes thereof. Accordingly, the probability analysis tool 754 may be used to distinguish between sensor noise, which may have a normal distribution, and sensor malfunction which may not be normally distributed. Each type of uncertainty may be handled differently due to the differences in their uncertainty distributions.

The probability analysis tool 754 may comprise any number of mathematical algorithms which are capable of analyzing the measured glucose values 640 and/or changes thereof and calculating a probability of glucose sensor accuracy $P_A$ 758. The probability analysis tool 754 may be also configured to receive other types of data on which the probability of glucose sensor accuracy $P_A$ 758 may be based, such as when the person eats a meal, when the person exercises, and when insulin is delivered to the person. In addition, $P_A$ 758 may be based on one or more measurements from an impedance measuring device coupled to the person and configured to measure impedance in the person. Such an impedance measuring device may indicate whether the glucose sensor 416 is properly coupled to the person and, thus, whether the measured glucose values 640 from the glucose sensor 16 are accurate. Other types of data may be used as well.

The probability analysis tool 754 can be take on a number of different forms such as a state machine, Bayesian models, or other algorithms. In one embodiment, the probability analysis tool 754 may take the form of a simple state machine, in which the probability of glucose sensor accuracy $P_A$ may always be in the set {0,1} (i.e., $P_A$ 758 is either 0% or 100%, depending on the state of the state machine). In this example, the system would transfer to a state of sensor inaccuracy, $T_{A \to I}$, if the $\Delta CG$ (i.e., the change in the current measured glucose value from the previous measured glucose value) is less than a certain negative threshold, $\tau_1$, and transfer back to a state of sensor accuracy, $T_{I \to A}$, if the $\Delta CG$ is greater than a certain positive threshold, $\tau_2$, or if the sensor CG value (i.e., the current measured glucose value) are within physiologically possible glucose values ($g_0$ and $g_{max}$) and a certain amount of time has elapsed since the transition to the state of sensor inaccuracy, $\Delta t_{A \to I} > \tau_3$. This may be represented mathematically as:

$T_{A \to I}$ if $\Delta CG < \tau_1$ $T_{I \to A}$ if $\Delta CG > \tau_2$ or ($g_0 < CG < g_{max}$ and $\Delta t_{A \to I} > \tau_3$)

If neither of these transfer conditions are met, then the state machine may remain in its current state. This is just one example of the probability analysis tool 754 taking the form of a state machine. The probability analysis tool 754 may take on other forms as well.

In another embodiment, the probability analysis tool 754 may comprise a hidden Markov model having two states for the glucose sensor: 1) The state wherein the glucose sensor is accurate, denoted by "$S_A$", and 2) The state wherein sensor is inaccurate, denoted by "$S_I$". The hidden Markov model may provide state transition functions that define the probability of transitioning from state $S_A$ to state $S_I$, such as the following function:

$$P_{A \to I} = \min\left[\left(1 - \frac{1}{1+e^{-(\Delta CG+\alpha_1)/\alpha_2}}\right) + \left(1 - \frac{1}{1+e^{-(CG+\alpha_3)/\alpha_4}}\right), 1\right],$$

where "CG" is the current measured glucose value, "$\Delta CG$" is the change from the previous measured glucose value to the current measured glucose value, and $\alpha_1$ to $\alpha_4$ are constants which depend on the characteristics of the glucose sensor. The range of output values for this function are zero to one, where zero represents 0% probability and one represents 100% probability of sensor accuracy. The "min" function takes the minimum value of the mathematical expression and the number one (i.e., 100%). This transition function may be based on the current CG and $\Delta CG$ values. Furthermore, the transition function may be a sigmoid, wherein the parameters $\alpha_1$ and $\alpha_3$ control the location of the sigmoid transition, and parameters $\alpha_2$ and $\alpha_4$ control the slope of the sigmoid. These parameters may be tuned for a specific patient and/or sensor batch.

Continuing with the example of the hidden Markov model, the probability of remaining in state $S_I$ (when the current state is $S_I$) may be $$P_{I \to I} = \max\left[\gamma P_{I_{k-1}} - \left(\frac{1}{1+e^{-(\Delta CG+\alpha_5)/\alpha_6}}\right), 0\right]$$

and is only a function of the $\Delta CG$ value and the previous probability $P_{I_{k-1}}$ of being in or transitioning to state $S_I$. The range of output values for this function are zero to one, where zero represents 0% probability and one represents 100% probability. The "max" function takes the maximum value of the mathematical expression and the number zero (i.e., 0%). The parameter "$\gamma$" is a decay term that is less than one and designed to gradually transition the state of the hidden Markov model back to $S_A$ if there is no evidence from the CG and $\Delta CG$ values to remain in $S_I$. The parameter $\gamma$ may be a constant and may be related to the probability of remaining in $S_I$ when $\Delta CG$ is relatively normal. For example, $\gamma$ may be selected so that the hidden Markov model remains in $S_I$ for approximately 10 minutes when $\Delta CG$ is relatively normal. This probability function also includes a sigmoid function that detects rapid rises in the CG signal that are associated with a return to $S_A$. The parameter $\alpha_5$ controls the location of the sigmoid transition, and parameter $\alpha_6$ controls the slope of the sigmoid. Both of these parameters may be tuned for a specific patient and/or sensor batch.

The current probability $P_I$ of transitioning to $S_I$ is either $P_{A \to I}$ or $P_{I \to I}$, depending on whether the current state is $S_A$ or $S_I$. The current probability $P_I$ of the glucose sensor being inaccurate (i.e., being is $S_I$) may be $(S_A \times P_{A \to I})+(S_I \times P_{I \to I})$. Note that the state ($S_A$ or $S_I$) is "1" when in that state and "0" otherwise. This includes the probability of transitioning to $S_I$ ($P_{A \to I}$) given the probability of being in $S_A$, and the probability of remaining in $S_I$ times the probability of currently being in $S_I$. The value of $P_{I \to I}$ is equal to $1-P_{I \to A}$, and the probability of the sensor being accurate is simply $P_A=1-P_I$. Thus, for this example, the probability of glucose sensor accuracy may be $$P_A = 1-[(S_A \times P_{A \to I})+(S_I \times P_{I \to I})].$$

Figure 8:
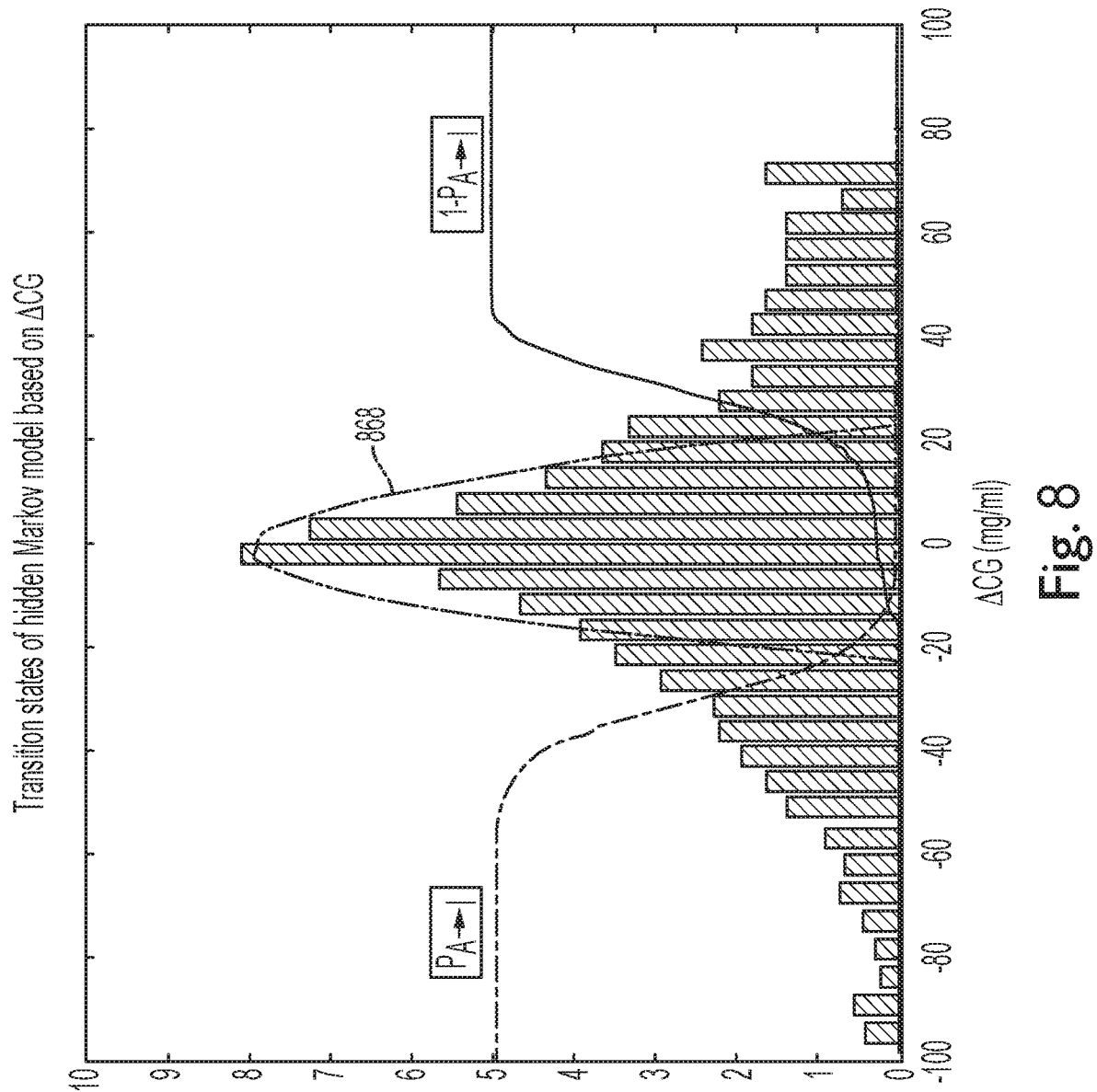
FIG. 8 depicts state transitions for the hidden Markov model according to at least one embodiment of the present disclosure.

FIG. 8 depicts a graphical representation of the two transition functions, $P_{A \to I}$ and $P_{I \to A}$ (i.e., $1-P_{I \to A}$, the probability of transitioning from $S_I$ to $S_A$ when the current state is $S_I$), over a histogram of $\Delta CG$. The histogram includes a Gaussian-shaped component 868 centered about zero with two tails associated with the transitions in and out of sensor malfunction. The two transition functions are plotted over the histogram to show that they may be tuned to trigger on the tails of the histogram. The Gaussian-shaped component 868 may represent the range of $\Delta CG$ values which may occur during normal operation of the glucose sensor. The $\Delta CG$ values located inside the Gaussian-shaped component 868 may be due to sensor noise, for example. The $\Delta CG$ values located outside and to the left of the Gaussian-shaped component 868 may be due to sensor transitioning from $S_A$ to $S_I$. The shape of this distribution may be used to characterize a batch of glucose sensors after production and used to code the sensors. That is, the transition functions ($P_{A \to I}$ and $P_{I \to A}$) may be adjusted (by adjusting $\alpha_1$ to $\alpha_6$ parameters) to correspond to the Gaussian-shaped component 868 for a particular batch of glucose sensors. Thus, the hidden Markov model may be used to determine the probability of sensor being accurate, $P_A$, based solely on the measured glucose values and changes thereof.

Figure 9:
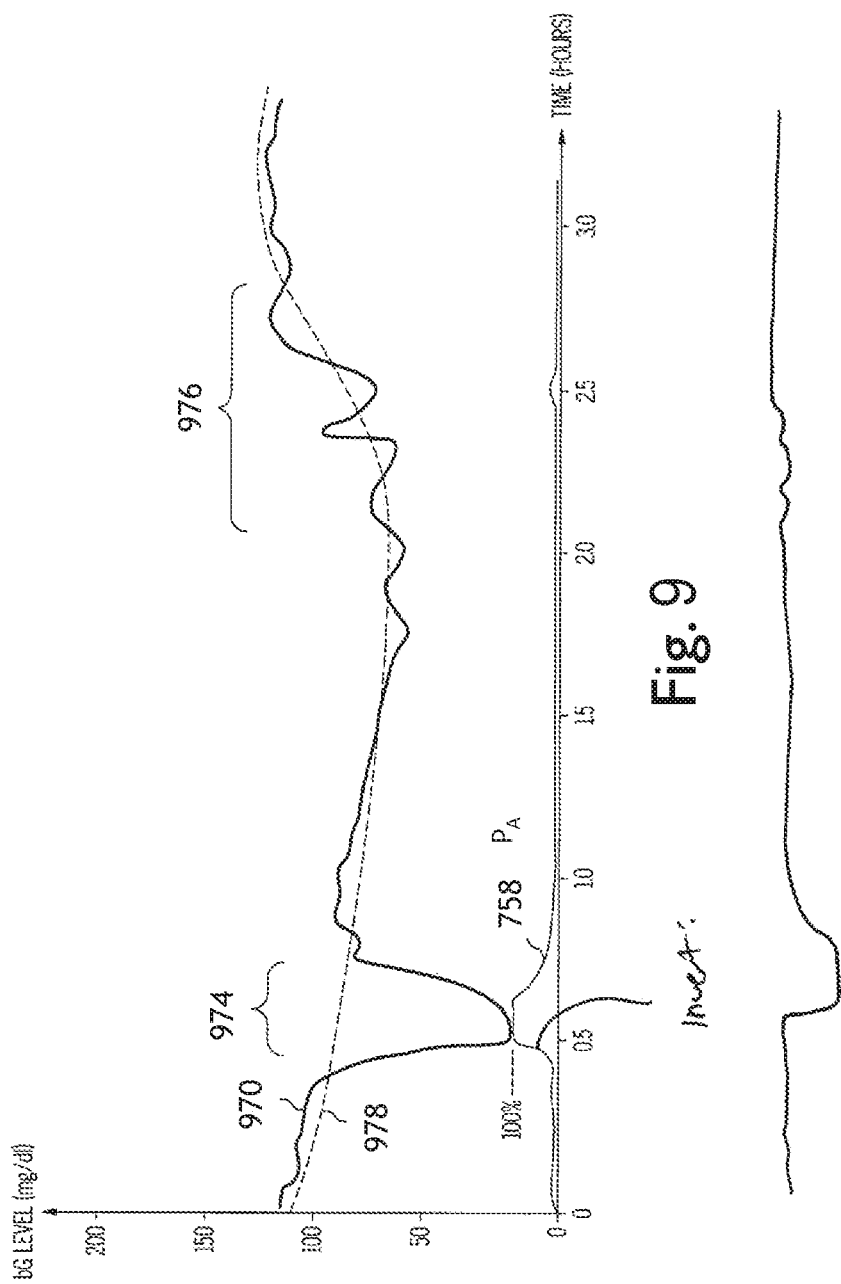
FIG. 9 depicts the operation of a hidden Markov model and a Kalman filter according to at least one embodiment of the present disclosure.

FIG. 9 illustrates a graph which shows an example of the operation of the hidden Markov model during glucose sensor malfunction and in the presence of glucose sensor noise. The graph includes the measured glucose values 640 and the probability of glucose sensor accuracy, $P_A$ 758. During time period 970, the glucose sensor may malfunction, thus causing the measured glucose values 640 to become inaccurate; at the same time, $P_A$ 758 (as determined by the hidden Markov model) may decrease from approximately 100% (before time period 970) to near 0% during time period 974. This may be due to the hidden Markov model's detection of the rapid decline in the value of the measured glucose values 640 at the beginning of time period 970 (i.e., when the malfunction first occurs). At the end of time period 974, the glucose sensor may begin to operate normally (i.e., the measured glucose values 640 become accurate again) and $P_A$ 758 may increase back to approximately 100% again. As before, this may be due to the hidden Markov model's detection of the rapid increase in the value of the measured glucose values 640 at the end of time period 974 (i.e., when the glucose sensor returns to normal operation). The rate of change of $P_A$ 758 from near 0% to approximately 100% may depend on how quickly the glucose sensor transitions from malfunctioning (inaccurate) to normal (accurate) operation. If the transition is relatively fast, $P_A$ 758 may transition quickly from near 100% to approximately 0%. However, if the glucose sensor transitions slowly from malfunctioning to normal operation, $P_A$ 758 may also transition slowly from near 0% to approximately 100%. The decay term $\gamma$ (found in the $P_{I \to I}$ equation)

may permit $P_A$ 758 to gradually transition back to $S_A$ if there is little or no evidence from the CG and ΔCG values to remain in $S_I$.

Referring still to FIG. 9, glucose sensor noise, which is shown as occurring during time period 976, may also cause $P_A$ 758 to decrease, depending on the severity and level of the noise. As depicted in FIG. 9, the glucose sensor noise during time period 976 may cause $P_A$ 758 to decrease slightly. Of course, both glucose sensor malfunction and sensor noise may have varying levels of amplitude and/or duration. Furthermore, glucose sensor malfunction and sensor noise may temporally overlap, either in part or completely. The hidden Markov model may be configured to determine $P_A$ 758 under any of these conditions. As will be discussed hereinafter, $P_A$ 758 may be used in a recursive filter in order to minimize the effect of glucose sensor malfunction so as to provide an accurate estimate the actual glucose level of the person in the presence of glucose sensor malfunction and/or sensor noise.

Referring again to FIG. 7, the system 750 for estimating the glucose level of a person having diabetes may comprise a recursive filter 752 which may be used to estimate the glucose level of the person, based on the plurality of measured glucose values weighted with the probability of glucose sensor accuracy $P_A$ 758. Examples of recursive filters which may be used include a Kalman filter and an Extended Kalman filter (EKF). Of course many other types of recursive filters may be used as well.

In one embodiment, the recursive filter 752 may be a Kalman filter (hereinafter references to a "Kalman filter" also apply to an "Extended Kalman filter") which is configured to process the measured glucose values 640 (i.e., the raw glucose sensor data) in a second-order linear system, as embodied in the equations below. The Kalman filter may comprise inter alia a state vector which represents the estimated state of the variable being estimated, which in this example is the glucose level of the person. The Kalman filter may include a prediction step, in which an a priori state and covariance are predicted, as wells as a measurement step, in which the a posteriori Kalman gain ($K_k$), the state vector, and the covariance are updated. The state vector may be updated every time a new input is received (i.e., recursively). In this disclosure, the variables in the state vector $x$ may represent an estimate of the person's actual glucose level, based on the measured glucose values 640. The estimated glucose level vector, $x$, may represent the estimated glucose level of the person, $g$; its first derivative, $\dot{g}$; and its second derivative, $\ddot{g}$. The measured glucose values vector, $z$, may include the current CG and ΔCG values. Other dynamic models may be used as well. The vectors $x$ and $z$ may be represented as $x_k=[g\ \dot{g}\ \ddot{g}]^T$ and $z_k=[CG\ \Delta CG]^T$, where $k$ represents $k$th sample. The following equation may be used to estimate the glucose level vector, $x$: $x_k=\hat{x}_k+K_k(z_k-H\hat{x}_k)P_A$, where $k$ represents the $k$th sample, $\hat{x}_k=Ax_{k-1}$, $K_k$ is the Kalman gain, and $P_A$ 758 is the probability of glucose sensor accuracy (from the probability analysis tool). In this fashion, the probability of sensor accuracy $P_A$ 758 may be used to weight the measured glucose values, embodied in the matrix $z_k$. The matrices and supporting equations for the Kalman filter may be as follows:

$$A = \begin{bmatrix} 1 & 1 & 0 \\ 0 & \beta_1 & 1 \\ 0 & 0 & \beta_2 \end{bmatrix}, Q = \begin{bmatrix} \sigma_g^2 & 0 & 0 \\ 0 & \sigma_g^2 & 0 \\ 0 & 0 & \sigma_g^2 \end{bmatrix}, H = \begin{bmatrix} 1 & 0 & 0 \\ 0 & 1 & 0 \end{bmatrix},$$

$$\hat{P}_k = AP_{k-1}A^T + Q_{k-1},$$

$$K_k = \hat{P}_k H^T (H\hat{P}_k H^T + R_k)^{-1},$$

$$P_k = (I - K_k H)\hat{P}_k,$$

$$R_k = \min\left[\sum_{i=1}^{\tau} \frac{(C_{k-i} - \overline{C})^2}{\tau - 1} + P_D \sigma_{max}^2, \sigma_{max}^2\right] + \sigma_{CG}^2,$$

$$C_{k-i} = CG_{k-i} - Hx_{k-i}, \text{ and}$$

$$\overline{C} = \frac{1}{\tau}\sum_{i=1}^{\tau} C_{k-i}.$$

The parameters $\beta_1$ and $\beta_2$ in matrix $A$ may be set to slightly less than one so that the estimated glucose level is damped when sensor malfunction occurs. The matrix $Q$ may represent the process noise covariance, while $K_k$ may represent the Kalman filter gain. Initial estimates for these parameters may be determined as is known in the art.

In the Extended Kalman filter (EKF), the system may be represented with a nonlinear model, $\hat{x}_k=f(x_{k-1}, u_k)$, and measurements are also represented with a nonlinear model, $z_k=h(x_k)$. This nonlinear model may include inputs from other sources, $u_k$, that may include meals, insulin, exercise or other inputs that may affect the glucose model. The nonlinear model may be derived from proprietary glucose physiological models. The prediction step is done by evaluating the nonlinear model, and the predicted uncertainty is calculated using the Jacobian of the model, $F_k$, with the state vector. This creates a localized linear model about the current system state. The following equations may be used by the EKF:

$$F_k = \begin{bmatrix} \frac{\partial f_1}{\partial x_1} & \cdots & \frac{\partial f_1}{\partial x_N} \\ \vdots & \ddots & \vdots \\ \frac{\partial f_N}{\partial x_1} & \cdots & \frac{\partial f_N}{\partial x_N} \end{bmatrix}$$

$$H_k = \begin{bmatrix} \frac{\partial h_1}{\partial x_1} & \cdots & \frac{\partial h_1}{\partial x_N} \\ \vdots & \ddots & \vdots \\ \frac{\partial h_M}{\partial x_1} & \cdots & \frac{\partial h_M}{\partial x_N} \end{bmatrix}$$

$$\hat{x}_k = f(x_{k-1}, u_k)$$

$$\hat{P}_k = F_k P_{k-1} F_k^T + Q_{k-1}$$

$$K_k = \hat{P}_k H_k^T (H_k \hat{P}_k H_k^T + R_k)^{-1}$$

$$P_k = (I - K_k H_k)\hat{P}_k$$

$$x_k = \hat{x}_k + K_k(z_k - h(\hat{x}_k))P_A.$$

After the prediction step, the current glucose sensor measurement, $CG_k$ may be used in the correction step. The correction step may also include the previously calculated probability of glucose sensor accuracy, $P_A$ 758 (from the probability analysis tool). The Kalman filter may be configured to weight the current measured glucose value with the probability of glucose sensor accuracy. For example, when $P_A$ 758 is low, the impact of the current measured glucose value on the Kalman filter may approach zero; conversely, when $P_A$ 758 is high, the impact of the current measured glucose value may be higher.

Distinguishing between sensor malfunction and sensor noise may facilitate estimating the glucose level of the person, and, as such, the Kalman filter may treat these situations differently. For normally distributed sensor noise, the Kalman filter may be configured to average out such noise. This may be due to the fact that sensor noise may be characterized for each type and/or batch of glucose sensors, including but not limited to the frequency range of the noise and the corresponding range of amplitude changes in the measured glucose values. These noise characteristics may be embodied in some or all of the parameters of the Kalman filter (e.g., in $\sigma_{max}^2$ or $\sigma_{CG}^2$) such that the Kalman filter is configured to filter out the noise and provide a relatively accurate estimated glucose level of the person, even in the presence of the sensor noise. On the other hand, sensor malfunction error is generally not normally distributed, so it should be handled differently within the Kalman filter framework. In one embodiment of the Kalman filter, $P_A$ 758 (determined by the probability analysis tool) may be used by the Kalman filter to weight the measured glucose values such that, when sensor malfunction occurs, the measured glucose values are largely ignored.

The covariance matrix from the Kalman filter represents the signal uncertainty, but does not include uncertainty caused by calibration. The uncertainty due to calibration should start high and decrease based on the number of glucose measurements as well as the difference between the glucose values and calibrated CGM pairs. To account for this uncertainty, the difference between the glucose and GCM should consider the Kalman filter covariance. With this modification, an error in the signal will not in most cases affect the uncertainty assigned to the calibration. Accordingly, in at least one embodiment the bolus calculator may be adjusted using the rate of change in glucose as well as the risk based calculation.

An example of the operation of a Kalman filter is shown in FIG. 9, which depicts the measured glucose values 970 and the estimated glucose level 978 of the person. As previously discussed, the probability of glucose sensor accuracy, $P_A$ 758, is shown as well. Normally, the person's estimated glucose level 978 may generally follow the measured glucose values 970. However, during time period 974, the sensor may malfunction; at the same time, $P_A$ 758 may decrease to near 0% (as determined by the operation of the probability analysis tool) so as to indicate a low probability of glucose sensor accuracy. Accordingly, the Kalman filter may take into account $P_A$ 758 so as to lessen the importance of the measured glucose values in estimating the glucose level of the person during the time period 974 of the sensor malfunction.

Continuing to refer to FIG. 9, the measured glucose values 970 may contain noise during time period 976. The Kalman filter may filter this noise so as to produce an estimated glucose level 978 which is relatively smooth during this time period 976. Although the measured glucose values may contain noise during time period 976, $P_A$ 758 may remain relatively high (e.g., near 100%) during this time since the probability analysis tool may be able to discern between sensor noise and sensor malfunction. As such, the Kalman filter may continue to place a relatively high importance on the measured glucose values during time period 972 (as evidenced by $P_A$ 758 being relatively high during time period 972).

The glucose sensor measurement uncertainty, $R_k$, is generally not constant. It may currently be estimated as a function of recent sensor measurements, z; the probability of glucose sensor accuracy, $P_A$; the maximum uncertainty of the measurement, $\sigma_{max}^2$; and the normal uncertainty associated with continuous glucose measurements, $\sigma_{CG}^2$. $\sigma_{max}$ may be calculated as the maximum physiological variance for glucose in a person with poorly controlled diabetes. It may be estimated from samples of CGM data. Similarly, $\sigma_{CG}$ is the minimal uncertainty for a glucose sensor when working properly. It may be the best case performance for a sensor and may be estimated by the variance of the measured glucose values compared to finger-stick data when the sensor is performing ideally. There may be other methods for estimating the measurement uncertainty that include using higher frequency glucose sensor data. This may be interpreted as the variance of the difference between recent past CG measurements and the estimated Kalman filter state.

The estimated glucose level of the person, as determined by the recursive filter, may be used to predict the glucose level of the person at some time in the future. These estimates may also be used to analyze the person's behavior and glucose patterns. Referring back to FIG. 7, a prediction algorithm 762 may be used to predict whether and/or when the person may become hypoglycemic and may provide associated alarms or warnings. The prediction algorithm 762 may receive the person's estimated glucose level 760 from the recursive filter 752 and may also receive the uncertainty of the estimated glucose level. However, the prediction algorithm 762 may be augmented with other input data, including meal times, carbohydrates, medications, exercise, insulin doses, and so forth. The prediction algorithm 762 may further receive information from other sources of data as well such as the measured glucose values (i.e., the raw glucose sensor data) or processed glucose sensor data. The prediction algorithm 762 may use Gaussian Process regression to learn a patient specific prediction model, indicated by the training model 764 in FIG. 7. The prediction algorithm 762 may also estimate the uncertainty of the prediction, which may allow the alarm thresholds to be adjusted for sensitivity. The alarm thresholds may also be adjusted based on the patient's current activity; for example, the sensitivity could be increased when the patient is sleeping.

As an example, the prediction of hypoglycemia can be done using the system model of the Kalman filter or the Extended Kalman filter. In this example the prediction step, $\hat{x}_k = Ax_{k-1}$ or $\hat{x}_k = f(x_{k-1}, u_k)$, is iterated for the desired prediction time and the predicted value is compared to the specific threshold. For example, if Kalman filter is updated every one minute, the prediction step may iterate the Kalman filter forty-five times in order to predict the glucose level of the person from the present to forty-five minutes in the future. The prediction model may include additional predicted inputs such as anticipated meals, insulin, exercise, or other anticipated future inputs.

In another example, the estimated glucose value, g, and rate-of-change of the glucose value, ġ, as estimated by the recursive filter are used to define a linear forecast which is compared to the hypoglycemia threshold and/or the hyperglycemia glucose threshold. The forecast is done with the following equation by multiplying the derivative by the desired prediction time, $t_{pt}$, to calculate the predicted glucose value, ĝ.

$$\hat{g} = g + \dot{g} t_{pt}$$

As an example, the specific input vectors used may include three samples of the estimated glucose levels (CG) taken at time t=0, −15, and −30 minutes, the current derivative of the estimated glucose level and the derivative at t=−15 minutes, and the time since the last meal. The meal information, $t_{meal}$, and bolus information, B, are optional and other data can also be included. This may be expressed mathematically as $$x_{CG}=[CG_{t=0}\ CG_{t=-15}\ CG_{t=-30}\ \Delta CG_{t=0}\ \ldots\ _{-15}\ \Delta CG_{t=-15}\ \ldots\ _{-30}]^T$$

$$x_{meal}=[CG_{t=0}\ CG_{t=-15}\ CG_{t=-30}\ \Delta CG_{t=0}\ \ldots\ _{-15}\ \Delta CG_{t=-15}\ \ldots\ _{-30}\ \min(t_{meal},t_{max})B]^T$$

Gaussian process regression may use the following equation to predict future glucose levels of the person based on training data, represented by (X,y), and the test point (x*, y*):

$$y^*=k(x^*,X)(k(X,X)+\mu I)^{-1}y,$$

where $k(x,x)$ is a covariance function. A Gaussian covariance function may be used to generate the results, but other functions can be used here as well. A Gaussian covariance function which may be used is:

$$k(\hat{x}, x) = \exp\left[-\frac{1}{2\sigma_k^2}\|\hat{x} - x\|^2\right].$$

Figure 10:
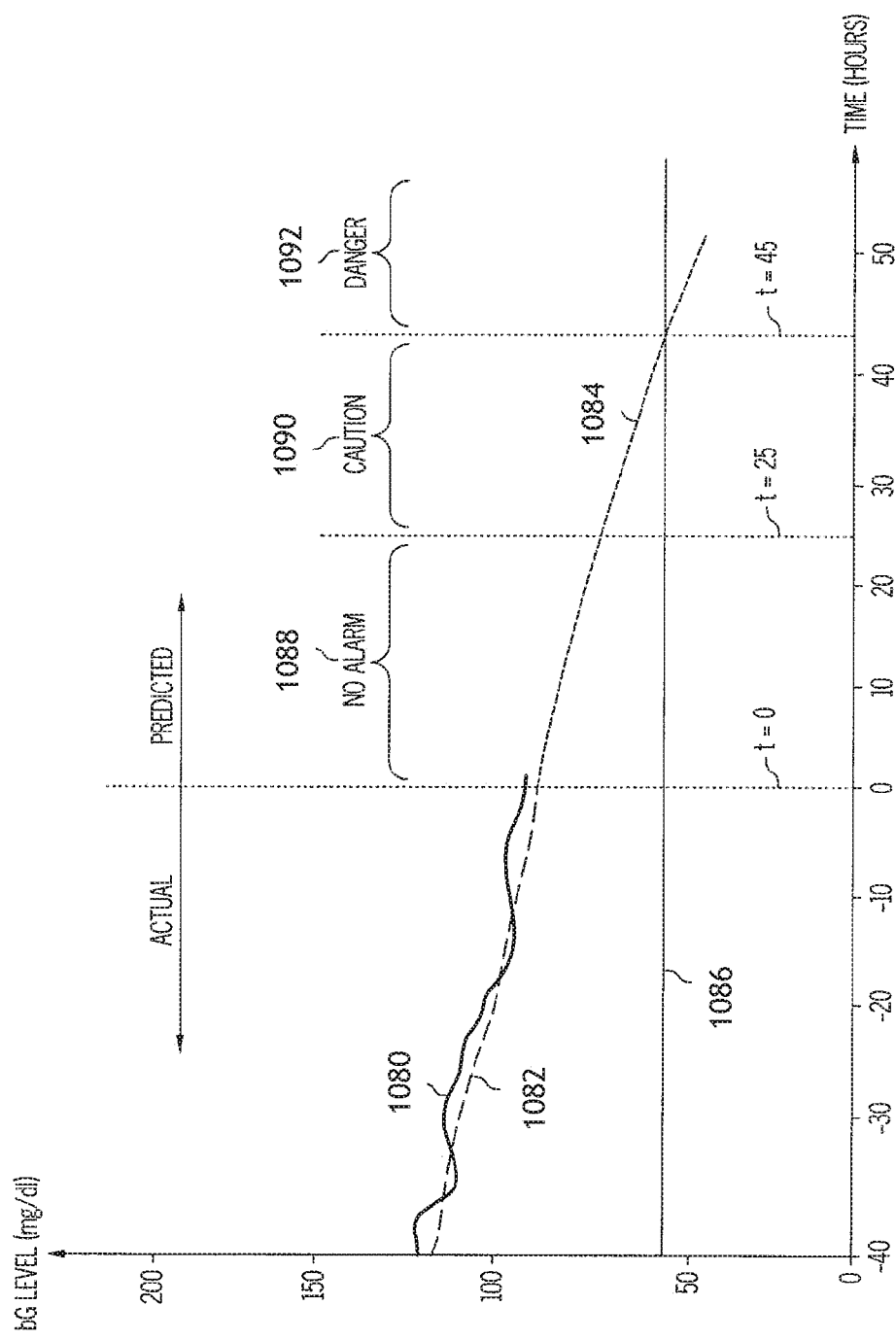
FIG. 10 depicts the operation of a prediction algorithm according to at least one embodiment of the present disclosure.

FIG. 10 depicts the operation of the prediction algorithm. The measured glucose values 1080 from the glucose sensor, and the estimated glucose level 1082 of the person (i.e., the output of the Kalman filter) are shown on the left (from a time t=−40 to 0). The current time is t=0. The prediction algorithm may determine the person's predicted glucose level 1080 at some time in the future (i.e., any time greater than t=0). Furthermore, the prediction algorithm may be used to predict whether and/or when the glucose level of the person may become hypoglycemic or hyperglycemic. A hypoglycemic threshold 1086 may be established for the person, such that an actual glucose level below this threshold means the person has become hypoglycemic. The hypoglycemic threshold 1086 may be uniquely determined for each person. The threshold for an average person may be about 50 mg/ml. Also the hypoglycemic threshold 1086 may vary for each person, such that the threshold is based on time, on an event, or combinations thereof. As examples, the hypoglycemic threshold 1086 for a person may depend on the time of day, whether the person has taken medication, whether and/or how long the glucose sensor is in the dropout state, and so forth. In FIG. 10, the prediction algorithm may predict that the person will become hypoglycemic at t=45 (i.e., 45 minutes from the current time). Of course, as time progresses, the prediction algorithm may continue to use the latest estimated glucose level (from the Kalman filter) and adjust the predicted glucose levels accordingly.

In addition to being able to predict future values of the glucose level of the person, the prediction algorithm may be further configured to determine the probability that the prediction is accurate. For example, predictions only one or two minutes in the future may be highly accurate, while predictions which are 60 or 70 minutes in the future may be relatively inaccurate. Of course the probability that the prediction is accurate may be a continuum, starting at near 100% for the immediate future and decaying to near 0% as the prediction reaches further into the future. This information may be used, in conjunction with the actual prediction itself, to provide a hypoglycemia warning system for the person. As shown in FIG. 10, the warning system may provide no alarm 1088 when the predicted glucose level 1082 is sufficient high above the hypoglycemic threshold 1086; it may advise caution 1090 when the predicted glucose level 1082 approaches within a predetermined range of the hypoglycemic threshold 1086; and it may advise danger 1092 when the predicted glucose level 1082 drops below the hypoglycemic threshold 1086.

The prediction algorithm, as previously discussed, may include a training function which learns the specific characteristics of a person. The training function may produce training data which may be used in the prediction algorithm and may be weighted based on the influence they have on generating the prediction. The level of influence the training data may be determined by the covariance function $k(x,x)$ used within the Gaussian Process regressor.

The prediction algorithm may be initialized with a generic set of training examples or no training examples. As new data are measured they may be incorporated into the prediction algorithm and/or training function. There are many possible algorithms for including new data. These include adding the data to the training set when 1) A predetermined period of time has elapsed, 2) The prediction failed on the specific data, 3) The input data is not represented in the training set, or 4) A patient or care provider manually includes the data, including all new data, if suitable.

When added to the training set, the new data can be included as a new vector, or by reweighing an existing training vector. The second method includes the benefit of maintaining constant memory needs. After adding additional data, the prediction algorithm may be updated immediately on the device, retrospectively on a personal computer, or retrospectively at a clinic.

Figure 11:
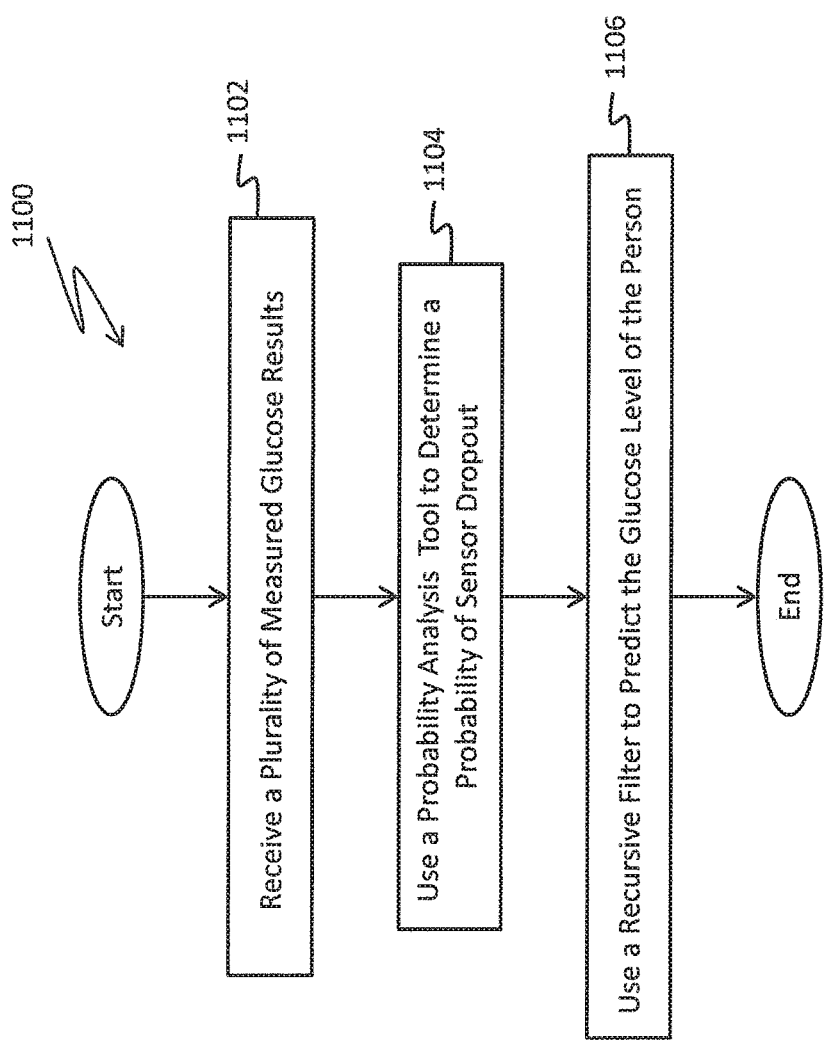
FIG. 11 depicts a method of predicting the glucose level of the person using a probability analysis tool and a recursive filter according to at least one embodiment of the present disclosure.

Referring to FIG. 11, a method 1100 is shown for estimating a glucose level of a person having diabetes. The method may comprise a number of acts, which may be performed in any suitable order. At act 1102, the method 1100 may receive into a computing device a plurality of measured glucose values from a glucose sensor coupled to the person. At act 1104, the method 1100 may use the computing device to analyze the plurality of measured glucose values with a probability analysis tool configured to determine a probability of glucose sensor accuracy based on the plurality of glucose measurements. At act 1106, the method 1100 may use the computing device to estimate a glucose level of the person using a recursive filter configured to weight the plurality of measured glucose values with the probability glucose sensor accuracy. The probability analysis tool and the recursive filter may be established as described hereinabove.

Insulin Bolus Calculator

Figure 12:
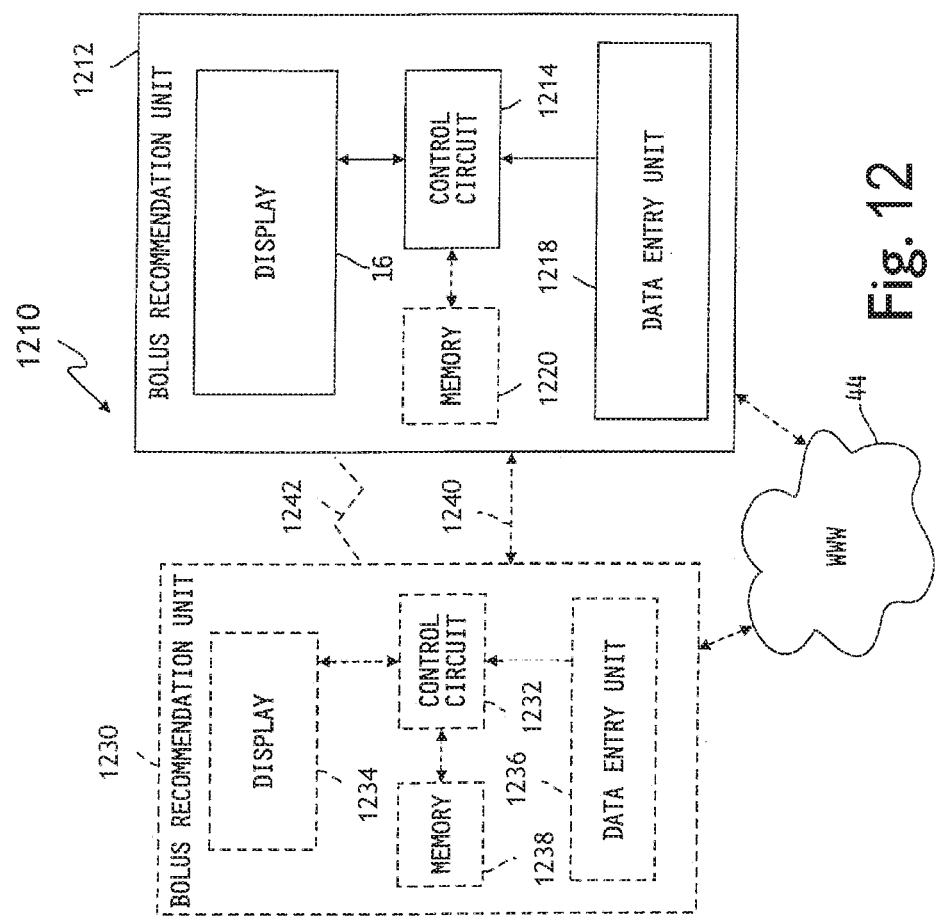
FIG. 12 is a block diagram of at least one illustrative embodiment of an insulin bolus recommendation system of the present disclosure.

Referring now to FIG. 12, a block diagram of one illustrative embodiment of an insulin bolus recommendation system 1210 is shown. In the illustrated embodiment, the insulin bolus recommendation system 1210 includes a bolus recommendation unit 1212 having at least a control circuit 1214 electrically connected to a visual display unit 1216 and also to a data entry unit 1218. The control circuit 1214 may illustratively be a conventional, microprocessor-based control computer capable of executing one or more software algorithms, although the control circuit 14 may alternatively be any single one or collection of electronic circuits capable of operation as described hereinafter. In some embodiments, the control circuit 1214 may be electrically connected to a conventional memory unit 1220 as shown in phantom. The visual display unit 1216 may be or include any conventional display screen including, but not limited to, a cathode ray tube (CRT) display, a liquid crystal display (LCD), a plasma display, a single or multicolor monitor, a touch-sensitive data entry screen, or the like. The data entry unit 1218 may be or include any conventional data input device including, but not limited to, a key board or key pad, a mouse or similar point-and-click device, one or more coded or non-coded, touch-sensitive switches associated with the display unit 1216, a voice-activated data input device, or the like.

The insulin bolus recommendation system 1210 may, in some embodiments, further include an additional bolus recommendation unit 1230 as shown in phantom in FIG. 12. The unit 1230 may include a control circuit 1232 electrically connected to a visual display unit 1234 and also to a data entry unit 1236, wherein the control circuit 1232, display unit 1234 and data entry unit 1236 may be provided in any of the forms described hereinabove with respect to the bolus recommendation unit 1212. The control circuit 1232 may further be electrically connected to a conventional memory unit 1238. In this embodiment, the bolus recommendation unit 1212 and the bolus recommendation unit 1230 may be each configured to share information via a wired connection 1240 including one or more signal paths physically connecting the two units, via a wireless signal path 1242 such as a radio signal or cellular telephone link, and/or via the world-wide-web (WWW) 1244, each using conventional technology.

The insulin bolus recommendation system 1210 is configured to determine and recommend administration of one or more specific insulin bolus quantities into the blood stream of a user of the system 1210 according to an insulin bolus recommendation protocol embodied in the system 1210 as one or more executable software algorithms. The physical structure of the insulin bolus recommendation system 1210 for executing such software algorithms and for communicating useful information between the system 1210 and the user may take various forms. In one illustrative embodiment, for example, the bolus recommendation system 1210 includes only the bolus recommendation unit 1212 embodied as a conventional personal computer (PC), laptop or notebook computer, personal data assistant (PDA) or the like, or as a hand-held, lap top or desk top application-specific bolus recommendation unit. In any of these cases, the bolus recommendation unit 1212 includes the memory unit 1220 having the number of executable software algorithms stored therein, and the control circuit 1214 is operable to execute these software algorithms to determine and recommend one or more injections of specific insulin bolus quantities into the blood stream of the user according to an insulin bolus recommendation protocol as will be described in detail hereinafter. In this embodiment, the display unit 1216 is controlled by the control circuit 1214 under the direction of the software algorithms to communicate information to the user and to prompt the user for information that the user may enter via the data entry unit 1218.

In another illustrative embodiment, the insulin bolus recommendation system 1210 includes the bolus recommendation unit 1212 and the bolus recommendation unit 1230. As one example of this embodiment, the bolus recommendation unit 1212 may be a PDA or application-specific bolus recommendation unit as described hereinabove, and the bolus recommendation unit 1230 may be a PC, laptop or notebook computer. In this embodiment, the unit 1212 may communicate with the unit 1230 either via the wireless interface 1242 or via the wired interface 1240 that may be electrically connected to a PDA or application-specific bolus recommendation unit cradle configured to receive the unit 1212 and electrically connect the unit 1212 in data communications with the unit 1230. In this example, the memory units 1220 and 1238 of the units 1212 and 1230 respectively may each have the number of software algorithms stored therein, and the user may use the bolus recommendation unit 1212 as a mobile insulin bolus recommendation unit and/or use the bolus recommendation unit 1230 as a stationary insulin bolus recommendation unit. In this case, the user will maintain the databases of each unit 1212 and 1230 current by periodically synchronizing the databases of both units 1212 and 1230 via the wired or wireless interface 1240 or 1242 respectively.

As another example of the embodiment of the insulin bolus recommendation system 1210 that includes the bolus recommendation unit 1212 and the bolus recommendation unit 30, the bolus recommendation unit 1212 may be a PDA, PC, laptop or notebook computer, cellular telephone or any other unit or device capable of accessing the WWW 1244. In this example, the bolus recommendation unit 1212 need not have the number of software algorithms stored in the memory unit 1220, and need not include the memory unit 1220 at all. The bolus recommendation unit 1230 may, in the example, be a remote computer or conventional web server also configured to access the WWW 1244 and having the number of software algorithms stored in the memory unit 1238. The control circuit 1232 of the remote computer or web server 1230 is operable in this example to execute the number of software algorithms based on information provided over the WWW 1244 by the user via the bolus recommendation unit 1212. In this particular embodiment, the user and/or a health care provider may access a web page or web site controlled by the bolus recommendation unit 1230 and provide the initial operating parameters and/or limits for the insulin bolus recommendation protocol to the control circuit 1232. The user may then and thereafter access the web page or web site and enter current blood glucose information, and the control circuit 1232 may then determine and recommend via the web page or web site one or more injections of specific insulin bolus quantities into the users blood stream, based on the current blood glucose information according to the insulin bolus recommendation protocol that will be described in detail hereinafter.

In this particular embodiment, the insulin bolus recommendation software algorithms thus reside in the remote computer or web server 1230, and in this regard the bolus recommendation unit 1212 need only include sufficient hardware so as to be capable of providing current blood glucose information to the web page or web site and of viewing the recommendation results produced on the web page or web site by the remote computer or web server 1230. As a practical matter, though, it may further be desirable in this embodiment to provide the bolus recommendation unit 1212 with the memory unit 1220 and store the number of bolus recommendation software algorithms therein so that the bolus recommendation unit 1212 may independently execute these software algorithms when it may not be possible or practicable to access the WWW 1244 and/or the appropriate web page or web site. It will further be desirable in such an embodiment to provide for the synchronization of the remote and/or web-based database with the database stored in the memory unit 1220 of the bolus recommendation unit 1212.

It will be appreciated that the insulin bolus recommendation system 1210 may be configured to cooperate with a glucose meter or other automatic blood glucose determination unit and/or an insulin pump or other automatic insulin dosing or administering unit. In embodiments wherein a glucose meter or other automatic blood glucose determination unit is included with the insulin bolus recommendation system 1210, the control computer 1214 may be configured to prompt such a unit, using conventional techniques, to automatically produce current blood glucose information which the system 1210 may then use, as will be described in detail hereinafter, to determine and recommend administering one more insulin bolus quantities. In embodiments wherein an insulin pump or other automatic insulin dosing unit is included with the insulin bolus recommendation system 1210, the control computer 1214 may be configured to prompt such a unit, using conventional techniques, to automatically administer recommended insulin bolus quantities to the user.

As described hereinabove, the insulin bolus recommendation system 1210 illustrated in FIG. 12 is operable to execute a number of software algorithms for determining and recommending administering of one or more of specific insulin bolus quantities into the blood stream of the user according to an insulin bolus recommendation protocol. The insulin bolus protocol, as it relates to the present disclosure, provides for the partitioning of an extended time period, e.g., one or more days, into a number of adjacent time intervals. With any such time interval, a specific target glucose level and a specific insulin sensitivity value may be defined. The target glucose level for any time interval corresponds to a constant glucose value within that time interval that the user would like to maintain. One example target glucose level may be 120 mg/dl, although the various target glucose levels defined in the number of time intervals may take on other values. The insulin sensitivity value for any time interval corresponds to the decrease glucose, e.g., in mg/dl per unit of infused insulin. One example insulin sensitivity value may be 30 mg/dl/U, although other insulin sensitivity values may alternatively be used. Details relating to example software algorithms suitable for execution by the system 1210 for carrying out such an insulin bolus protocol are described in U.S. patent application Ser. No. 10/927,614, which is assigned to the assignee of the subject invention, and the disclosure of which is incorporated herein by reference. It should be understood, however, that the system 1210 may alternatively or additionally be programmed to execute other conventional software algorithms for carrying out such an insulin bolus protocol.

Figure 13:
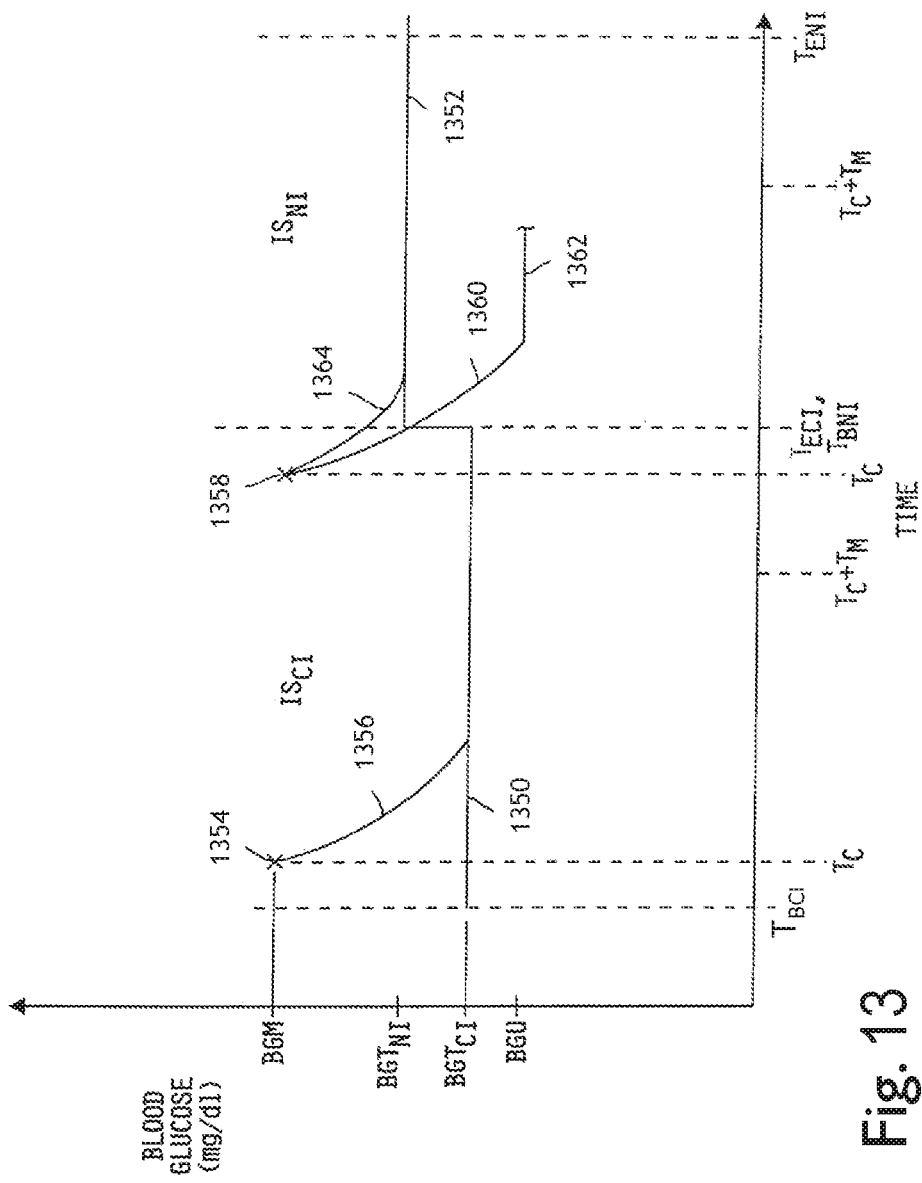
FIG. 13 is a plot of blood glucose vs. time illustrating a number of examples of insulin bolus administration relative to a current and next adjacent time interval.

Referring now to FIG. 13, a plot of blood glucose vs. time is shown illustrating two time intervals according to the above-described insulin bolus protocol. A current time interval begins at a "begin current interval" time, $T_{BCI}$, and ends at a subsequent "end current interval" time, $T_{ECI}$. The target blood glucose 1350 defined during the current interval is designated $BGT_{CI}$, and the insulin sensitivity defined during the current interval is designated $IS_{CI}$. A next adjacent time interval begins at a "begin next interval" time, $T_{BNI}$, which coincides with the "end current interval" time, $T_{ECI}$, and ends at a subsequent "end next interval" time, $T_{ENI}$. The target blood glucose 1352 defined during the next adjacent interval is designated $BGT_{NI}$, and the insulin sensitivity defined during the next adjacent interval is designated $IS_{NI}$.

The user of the system 1210 may, at any time, obtain a measurement of the user's glucose level via one or more conventional techniques. If the current measurement of the user's glucose level exceeds the target blood glucose level for the current interval, $BGT_{CI}$, conventional bolus recommendation systems are typically operable to compute a recommended correction insulin bolus, CB, according to the equation:

$$CB = (BGM - BGT_{CI})/IS_{CI}, \quad (4)$$

where BGM is the blood glucose level measured at the current time, $T_C$. The user then administers the recommended correction insulin bolus near the time $T_C$, and the administered insulin bolus functions in a known manner to lower the glucose level over a time period $T_M$, where $T_M$ is defined for purposes of this document as the duration of the glucose lowering action of an administered insulin bolus.

Referring again to FIG. 13, the foregoing scenario is illustrated in the current interval where a blood glucose value 1354 is measured at the current time, $T_C$. With a correction bolus, CB, computed as just described administered near $T_C$, the blood glucose decreases 1356 over time in this example to the target glucose value 1350, which corresponds to the target blood glucose value for the current interval, $BGT_{CI}$, and remains at $BGT_{CI}$ for the duration $T_M$. Using a numerical example, assume that the measured blood glucose value, BGM, corresponding to point 1354, is 200 mg/dl, the target blood glucose value during the current interval, $BGT_{CI}$, is 120 mg/dl, and the insulin sensitivity during the current interval, $IS_{CI}$, is 30 mg/dl/U. Substituting these numbers into the conventional correction bolus equation described above yields (200 mg/dl−120 mg/dl)/30 mg/dl/U=2.667, or approximately 2.7 units. Thus, during the current interval, it takes approximately 2.7 units of insulin to lower the user's glucose level from 200 mg/dl to the target 120 mg/dl.

As illustrated in the example just given, the conventional correction bolus equation works well as long as the correction bolus is administered sufficiently early in the current time interval so that the duration of the glucose lowering action of the administered insulin bolus, $T_M$, is confined to the current interval. However, using the conventional correction bolus equation as a basis for computing and administering a correction bolus at a current time, $T_C$, that occurs later in the current time interval, so that the duration of the glucose lowering action of the administered bolus, $T_M$, spans the current and next adjacent time intervals, may yield undesirable results. For example, consider the case where a blood glucose value 58 is measured at the now current time, $T_C$, near the end, $T_{ECI}$, of the current time interval (corresponding to the beginning time, $T_{BNI}$, of the next adjacent time interval). With a correction bolus, CB, computed using the conventional equation described above and administered near $T_C$, the blood glucose decreases over time 1360, in this example, into the next adjacent time interval and to a glucose level 1362 that may be significantly below the target glucose value 1352 of the next adjacent time interval. Using another numerical example, assume that the measured blood glucose value, BGM, corresponding to point 1358, is again 200 mg/dl, the target blood glucose value during the current interval, $BGT_{CI}$, is again 120 mg/dl, the insulin sensitivity during the current interval, $IS_{CI}$, is again 30 mg/dl/U, the target blood glucose value during the next adjacent time interval, $BGT_{NI}$, is 150 mg/dl and the insulin sensitivity during the next adjacent time interval, $IS_{NI}$, is 40 mg/dl/U. Since $T_C$ is still in the current time interval, the conventional correction bolus equation described above again yields (200 mg/dl−20 mg/dl)/30 mg/dl/U=2.667, or approximately 2.7 units. However, suppose that $T_C$ in this example is within one minute of $T_{BNI}$. If the user had waited another minute to take the blood glucose measurement, so that the next adjacent time interval was now the current time interval, the conventional correction bolus equation described above would have yielded (200 mg/dl−150 mg/dl)/40 mg/dl/U=1.25, or approximately 1.3 units. Administering a 2.7 mg/dl insulin bolus at or near $T_C$ in this example, thus results in unnecessary insulin in the amount of 1.4 units which, at an insulin sensitivity, $IS_{NI}$, of 40 mg/dl/U results in a blood glucose undershoot 1362 of (40 mg/dl/U*1.4 U)=56 mg/dl below the blood glucose target 1352, corresponding to a final glucose reduction from 200 mg/dl at point 1358 to 94 mg/dl at 1362.

One effective technique for improving the accuracy of the correction bolus determination in cases where the time duration, $T_M$, of the glucose lowering action of the administered insulin bolus spans the current and the next time interval is to take into account the time-dependent nature of the target glucose level and of the insulin sensitivity. For example, if $h(\tau)$ is the relative amount of insulin activity used up for a bolus of insulin (of a given type) administered at $\tau=0$. At $\tau \geq T_M$, $h(\tau)=1$. If $IS(T)$ is then the insulin sensitivity as a function of time, then at the current time, $T=T_C$, a unit bolus of insulin has the following impulse response:

$$H(T, t_C) = \int_0^{T-T_C} h(\tau) \cdot IS(T_C + \tau) \cdot d\tau, \quad (5)$$

where $h(\tau)$ is the time derivative of $h(\tau)$.

If $D(T)$ is the time-dependent insulin bolus infusion rate function, the glucose drop at a given time relative to $BG_{-\infty}=BG(T \to -\infty)$ yields:

$$\Delta BG(T) = \int_{-\infty}^{T} D(T_C) \cdot \int_0^{T-T_C} h(\tau) \cdot IS(T_C + \tau) \cdot d\tau \cdot dT_C. \quad (6)$$

To calculate at the time $T=T_{BNI}$ the blood glucose drop $\Delta BG_{pb}$ that will happen in the future caused by the already administered past insulin boli, the following equation is used:

$$\Delta BG_{pb}(T_{BNI}) = \quad (7)$$
$$\int_{T_{BNI}-T_M}^{T_{BNI}} D(T_C) \cdot \int_{T_{BNI}-T_C}^{T_{BNI}-T_C+T_M} h(\tau) \cdot IS(T_C + \tau) \cdot d\tau \cdot dT_C.$$

To calculate a correction bolus amount, CB, to be given at a time $T=T_C + \epsilon$ with a bolus infusion duration that is negligible against $T_M$, the following equation is used:

$$CB = (\Delta BG_{needed} - \Delta BG_{pb}(T_{BNI})) \bigg/ \int_0^{T_M} h(\tau) \cdot IS(T_{BNI} + \tau) \cdot d\tau. \quad (8)$$

The needed BG drop, $\Delta BG_{needed}$, must therefore be calculated based on the target blood glucose value at $T=T_{BNI}+T_M$, or $BGT_{NI}$. Combining the results of (4), (5) and (8), the equation for computing a correction bolus amount, CB, when the time duration spans the current and next time intervals is thus given by:

$$CB = (BGM - BGT_{NI}) \bigg/ \bigg[ \quad (9)$$
$$\left(IS_{CI} * \int_0^{T_{BNI}-T_C} h(\tau)d\tau\right) + \left(IS_{NI} * \int_{T_{BNI}-T_C}^{T_M} h(\tau)d\tau\right)\bigg].$$

Solving (9) for the integrals yields the equation:

$$CB = (BGM - BGT_{NI})/\{[IS_{CI} * (h(T_{BNI}-T_C) - h(0))] + [IS_{NI} * (h(T_M) - h(T_{BNI}-T_C))]\} \quad (10),$$

wherein the quantity $(h(T_{BNI}-T_C)-h(0))$ corresponds to the fraction or percentage of the insulin action of the bolus given at or near $T=T_C$ that will be spent or used to lower the measured blood glucose value, BGM, during the current time interval, and the quantity $(h(T_M)-h(T_{BNI}-T_C))$ corresponds to the fraction or percentage of the insulin action of the bolus given at or near $T=T_C$ that will be spent or used to lower the measured blood glucose value, BGM, during the next adjacent time interval.

Referring again to FIG. 13, another numerical example will be used to illustrate the effect of equation (10) on the blood glucose measurement value 1358. Assume that the measured blood glucose value, BGM, corresponding to point 1358, is again 200 mg/dl, the target blood glucose value during the current interval, $BGT_{CI}$, is again 120 mg/dl, the insulin sensitivity during the current interval, $IS_{CI}$, is again 30 mg/dl/U, the target blood glucose value during the next adjacent time interval, $BGT_{NI}$, is again 150 mg/dl and the insulin sensitivity during the next adjacent time interval, $IS_{NI}$, is again 40 mg/dl/U. Also assume that at $T=T_{BNI}$, 40% of the insulin action of an insulin bolus given at or near $T=T_C$ (corresponding to point 1358) will have been spent to lower the glucose level during the current time interval. This leaves 1−0.4=60% of the insulin action of the insulin bolus given at or near $T=T_C$ to be spent lowering the glucose level during the next adjacent time interval. According to equation (10) then, the correction bolus, CB, that should be administered at or near $T_C$ (corresponding to point 1358) is CB=(200 mg/dl−50 mg/dl)/[(30 mg/dl/U*0.4)+(40 mg/dl/U*0.6)]=1.388 U, or approximately 1.4 U. With an insulin sensitivity during the next adjacent time interval of 40 mg/dl/U, administering 1.4 U of insulin at $T=T_C$ (corresponding to point 1358) results in a decrease 1364 in blood glucose of (40 mg/dl/U)*1.4 U=56 mg/dl, corresponding to a decrease in blood glucose from 200 mg/dl at point 58 to a final glucose level 1366 of approximately 144 mg/dl, which is much closer to the target blood glucose in the next adjacent time interval of 150 mg/dl than the 94 mg/dl resulting from use of the conventional correction bolus equation (4).

Figure 14:
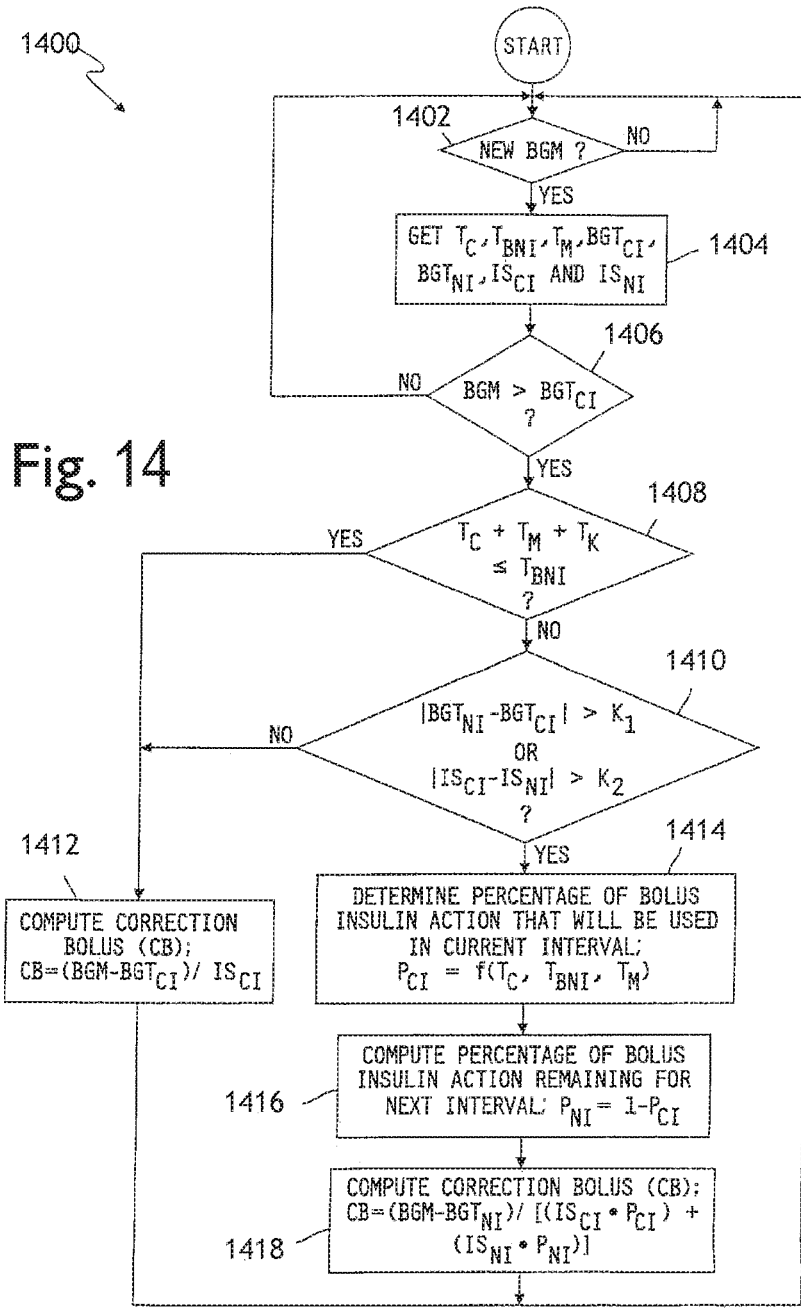
FIG. 14 is a flowchart of at least one embodiment of an insulin bolus recommendation software algorithm, executable by the system of FIG. 12, for determining and recommending insulin bolus quantities of the present disclosure.

Referring now to FIG. 14, a flowchart is shown of one illustrative embodiment of a software algorithm 1400 for determining recommended insulin bolus quantities under the various conditions presented by the foregoing examples. The insulin bolus recommendation software algorithm 1400 of FIG. 14 will be described as being implemented with the insulin bolus recommendation unit 1212 and executed by the control circuit 1214, wherein the insulin bolus recommendation unit 1212 is provided in the form of a conventional PDA or a hand-held, application-specific insulin bolus recommendation unit, although those skilled in the art will recognize that the algorithm 1400 may alternatively be implemented with the bolus recommendation unit 1212 and/or bolus recommendation unit 1230 provided in any one or more of the physical forms described hereinabove.

In the illustrated embodiment, the algorithm 1400 begins at step 1402 where the control circuit 1214 is operable to determine whether a new measured glucose value, BGM, is available. The algorithm 1400, in the exemplary embodiment, presumes that glucose measurements taken at any current time, $T_C$, will be entered into, or otherwise be obtained, by the system 1210 at or near the time $T_C$. Until a new glucose value, BGM, is received, the control circuit 1214 will continue to loop back to the start of step 1402. Otherwise when a new glucose measurement, BGM, becomes available, algorithm execution advances to step 1404 where the control circuit is operable to obtain the necessary parameters relating to the current and next adjacent time intervals. In one embodiment, the necessary parameters are stored in the memory unit 20 and/or within the executable memory of the control circuit 1214, and the control circuit 1214 is operable to execute step 1404 by retrieving these parameters from the memory unit 1220 and/or from the executable memory of the control circuit 1214. Alternatively, the necessary parameters may be entered into or otherwise provided to the system 1210 using any one or more of the components described hereinabove with respect to FIG. 12. In any case, the necessary parameters obtained at step 1404 in the exemplary embodiment include the current time value, $T_C$, the beginning time value of the next adjacent time interval, $T_{BNI}$, the time duration, $T_M$, of the glucose lowering action of the insulin bolus to possibly be administered at or near $T_C$, the glucose measurement value, BGM, the glucose target of the current time interval, $BGT_{CI}$, the glucose target of the next adjacent time interval, $BGT_{NI}$, the insulin sensitivity of the current time interval, $IS_{CI}$, and the insulin sensitivity of the next adjacent time interval, $IS_{NI}$.

Following step 1404, the control circuit 1214 is operable at step 1406 to compare the measured glucose value, BGM, to the glucose target value of the current time interval, $BGT_{CI}$. If BGM does not exceed $BGT_{CI}$, execution of the algorithm 1400 loops back to the beginning of step 1402, otherwise the algorithm execution advances to step 1408. Thus, the algorithm 1400 does not advance past step 1406 unless and until a new glucose measurement, BGM, is available and BGM exceeds $BGT_{CI}$. It will be understood that the algorithm 1400 may be incorporated into another insulin bolus recommendation algorithm that is operable to execute steps 1402 and 1406. In such cases, the algorithm 1400 may be modified to be accommodated by such an insulin bolus recommendation algorithm by omitting steps 1402 and 1406.

At step 1408, the control circuit 1214 is operable to compare a sum of $T_C$, $T_M$ and a constant time value, $T_K$, to the beginning time of the next adjacent time interval, $T_{BNI}$. If this sum is greater than $T_{BNI}$, algorithm execution advances to step 1410. Otherwise, if this sum is less than or equal to $T_{BNI}$, algorithm execution advances to step 1412. In one embodiment, $T_K$ is zero, and the sum of $T_C$ and $T_M$ represents the time value, relative to the current and next adjacent time intervals, that the insulin activity of a bolus, if administered at the current time, $T_C$, would be complete. Thus, if the sum of $T_C$ and $T_M$ is less than or equal to $T_{BNI}$, this indicates that $T_C$ is early enough in the current time interval that the time duration, $T_M$, of the glucose lowering action of an insulin bolus administered at time $T_C$ is confined to the current time interval. In this case, the computation of an accurate value of a correction bolus, CB, may be accomplished using the conventional equation (4). On the other hand, if the sum of $T_C$ and $T_M$ exceeds $T_{BNI}$, this indicates that $T_C$ is late enough in the current time interval that the time duration, $T_M$, of the glucose lowering action of an insulin bolus administered at time $T_C$ spans the current and the next adjacent time intervals. In this case, the computation of an accurate value of a correction bolus, CB, must be accomplished using the correction bolus equation (10) as described hereinabove. Embodiments of the algorithm 1400 are contemplated in which the control circuit 1214 is operable to compute a correction bolus, CB, according to equation (10) only if the time duration, $T_M$, of the glucose lowering action of the correction bolus to be administered at time $T_C$ extends into the next adjacent time interval by a predefined time amount. In such embodiments, the time constant $T_K$ will not be zero, but will instead be some positive time value that ensures that the inequality of step 1408 does not lead to step 1410 unless $T_M$ extends into the next adjacent time interval by the predefined time amount. As one specific example, the predefined time amount may be 30% of $T_M$, although it will be understood that other values of the predefined time amount may be used.

In any case, if the control circuit 1214 determines at step 1408 that the time duration, $T_M$, of the glucose lowering action of the correction bolus to be administered at time $T_C$ extends sufficiently into the next adjacent time interval, algorithm execution advances to step 1410 where the control circuit is operable to compare an absolute value of a difference between $BGT_{CI}$ and $BGT_{NI}$ with a constant, K1, and to compare an absolute value of a difference between $IS_{CI}$ and $IS_{NI}$ with another constant, K2. In one embodiment, K1 and K2 are both zero, and the absolute values of the differences yield zero only if the target glucose and insulin sensitivity values do not change between the current and next adjacent time intervals. In this case, the computation of an accurate value of a correction bolus, CB, may be accomplished using the conventional equation (4). On the other hand, if either one or both of the target glucose or the insulin sensitivity values change between the current and next adjacent time intervals, the computation of an accurate value of a correction bolus, CB, must be accomplished using the correction bolus equation (10) as described hereinabove. Embodiments of the algorithm 1400 are contemplated in which the constant values K1 and K2 are set at some positive constant values to thereby require the target glucose and/or the insulin sensitivity values to change by more than predefines amounts before computing the correction bolus, CB, according to equation (10). As one specific example, K1 and K2 may both be 5, although it will be understood that other values of K1 and K2 may be used wherein K1 may or may not be equal to K2.

In any case, if the time duration, $T_M$, of the glucose lowering action of an insulin bolus to be administered at time $T_C$ will be confined to the current time interval or at least not extend sufficiently into the next adjacent time interval, and neither of the glucose target values nor the insulin sensitivity values has changes significantly between the current and next adjacent time intervals, the control circuit 1214 is operable at step 1412 to compute the correction bolus, CB, according to equation (4) such that CB=(BGM−$BGT_{CI}$/$IS_{CI}$. If, on the other hand, the time duration, $T_M$, extends sufficiently into the next available time interval, or either one or both of the glucose target value and the insulin sensitivity value change significantly between the current and next available time intervals, the control circuit 1214 is operable at step 1414 to determine the fraction or percentage, PU, of bolus insulin action that will be used or spent lowering the glucose level in the current time interval.

In the illustrated embodiment, the control circuit 1214 is operable to determine this fraction or percentage as a function of the current time, $T_C$, the beginning time of the next adjacent time interval, $T_{BNI}$, and the time duration, $T_M$, of the glucose lowering action of the correction bolus that will be administered at or near $T_C$. This function may be stored in the memory unit 1220 in the form of one or more tables, graphs, charts, equations or the like, and in one specific embodiment this function is stored in the memory unit 1220 in the form of a two-dimensional look up table. In this embodiment, the look up table has as one table axis time values corresponding to the difference between $T_{BNI}$ values and $T_C$ values and another table axis time duration values, $T_M$. The table is populated, in this embodiment, with percentage values, corresponding to percentages of bolus insulin action that will be used or spent lowering the glucose level in the current time interval, as functions of $T_M$ values and of time difference values, corresponding to $T_{BNI}-T_C$. Thereafter at step 1416, the control circuit is operable to determine the fraction or percentage, PR, of bolus insulin action that will be used or spent lowering the glucose level in the next adjacent time interval by subtracting the percentage determined at step 1414, with respect to the current time interval, from 100%.

Those skilled in the art will recognize that the steps 1414 and 1416 may alternatively be modified so that the control circuit 1214 is operable to compute the fraction or percentage, PR, of bolus insulin action that will be used or spent lowering the glucose level in the next adjacent time interval as a function of $T_C$, $T_{BNI}$ and $T_M$ using any of the techniques described hereinabove with respect to step 1414, and to then determine the fraction or percentage, PU, of bolus insulin action that will be used or spent lowering the glucose level in the current time interval by subtracting the percentage determined at step 1414, with respect to the next adjacent time interval, from 100%.

In any case, algorithm execution advances from step 1416 to step 1418 where the control circuit 1214 is operable to compute the correction bolus quantity, CB, according to equation (10) such that CB=(BGM−BGT$_{NI}$)/[IS$_{CI}$*PU]+ (IS$_{NI}$*PR)]. Algorithm execution loops back from either of steps 1412 or 1418 to the beginning of step 1402.

In an embodiment of the bolus calculator, the calculator may provide a reduction in the insulin dose based on the glucose rate-of-change. If glucose is decreasing, then a predicted glucose value may be used in the bolus calculator. The predicted glucose value may be calculated using a linear prediction or with another model. This model may be a physiological model. Typically the correction dose of a bolus calculation is based on the deviation between the current glucose value and a glucose target. In one embodiment, the correction dose ($I_C$) may be determined with the equation $$I_c = \frac{1}{c}(g - g_t)$$

In such an equation, c is the correction factor, g is the glucose level, and $g_t$ is predicted glucose level at time t.

In the case where the rate of change is known, and is negative, then this calculation can be changed to use the predicted value. In the following case a linear model is used to determine the predicted glucose value.

$$I_c = \frac{1}{c}(g + \dot{g}\tau - g_t)$$

In this case τ is the prediction time and may be set depending on the PwD's personal aversion and awareness of hypoglycemia. In at least one embodiment, a range of about 20 minutes to about 60 minutes may be used for the prediction time.

In the case where the risk method is used, then the correction dose uses the following equation, where $g_{adj}$ is the adjustment to the maximum allowed glucose.

$$Ic = \frac{1}{c}(g - (g_t + g_{adj}))$$

If the recommended negative correction dose is greater than the meal bolus such that the sum of the two is negative, then the system may recommend that the PwD increases the amount of carbohydrates in the meal to account for the difference. Alternatively, the system may also reduce the basal rate to account for the difference.

EXAMPLES

Figure 15:
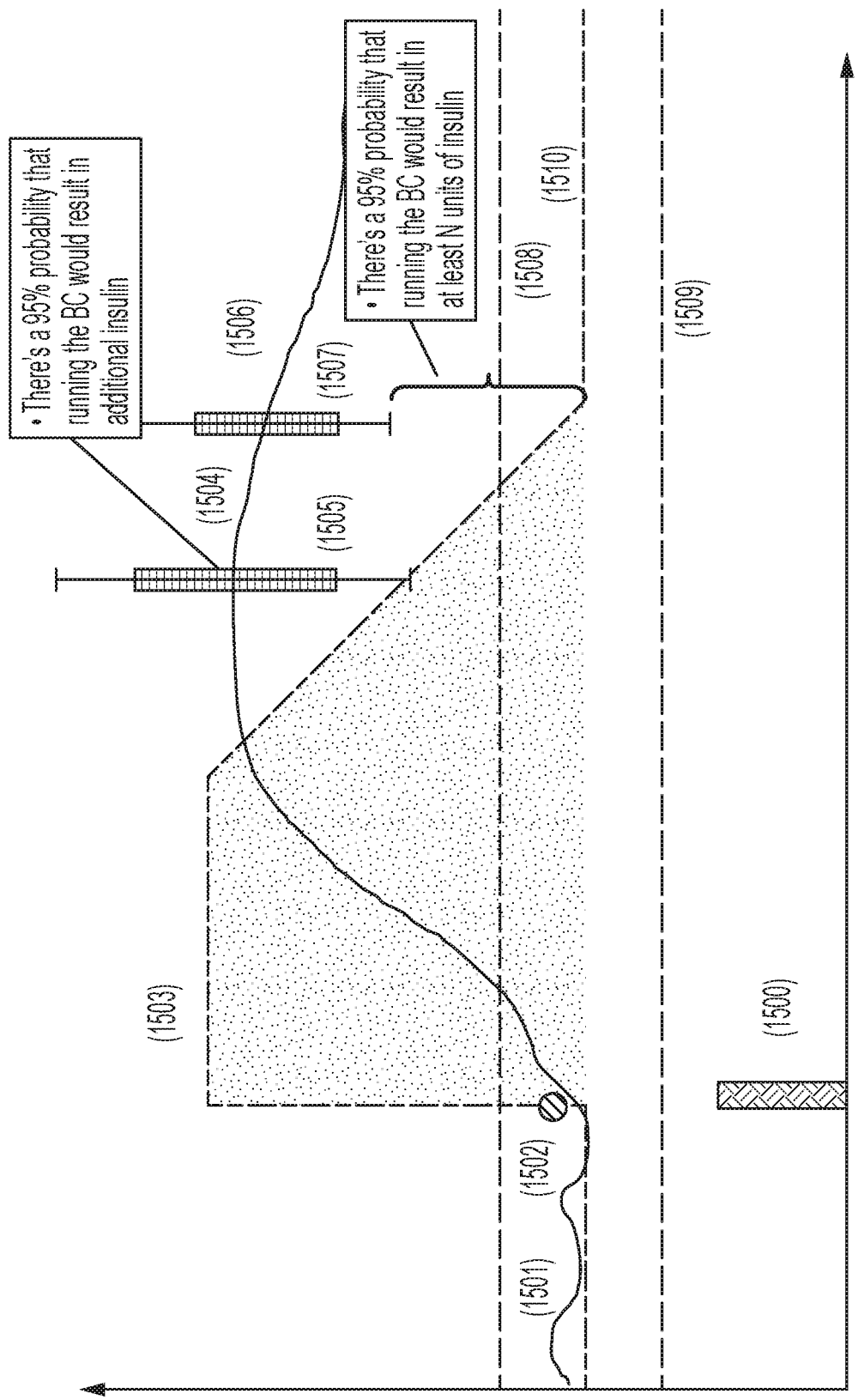
FIGS. 15-18 show examples of CGM data and the resulting response of at least one embodiment of methods of the present disclosure.

FIGS. 15-18 show examples of embodiments of the present disclosure where CGM glucose data is evaluated under at least one embodiment of a method of the present disclosure. In FIG. 15, a post-prandial CGM data set is evaluated and results in an alert being given. As shown in at least some of FIGS. 15-18, labels include: Meal intake 1500, CGM trace 1501, CMBG measurement 1502, SMBG that results in a correction bolus 1502*b*, Post-prandial trapezoid of the max allowable glucose 1503, Max Allowable Glucose elevated due to the correction dose 1503*b*, CGM value 1 1504, Uncertainty associated with CGM value 1 1505, CGM value 2 1506, Uncertainty associated with CGM value 2 1507, Upper target 1508, Lower target 1509, Target 1510, CGM value 1511, Uncertainty associated with the corresponding CGM value 1512, Hypo prediction 1513, Predicted glucose value based on a model 1514, CGM trace with a rate-of-change of zero at meal time 1515, CGM trace with a negative rate-of-change at meal time 1516, Modified correction bolus is based on the predicted glucose value 1517, and Prediction time, 1518.

In FIG. 15, the CGM signal remains high after the post-prandial trapezoid associated with the meal rise. If the value for $I_0$ was set to 0, then an alarm would register at CGM value 1 (1504). If, however, a minimum insulin dose was set to N, then the system would not alarm until CGM value 2 (1506).

Figure 16:
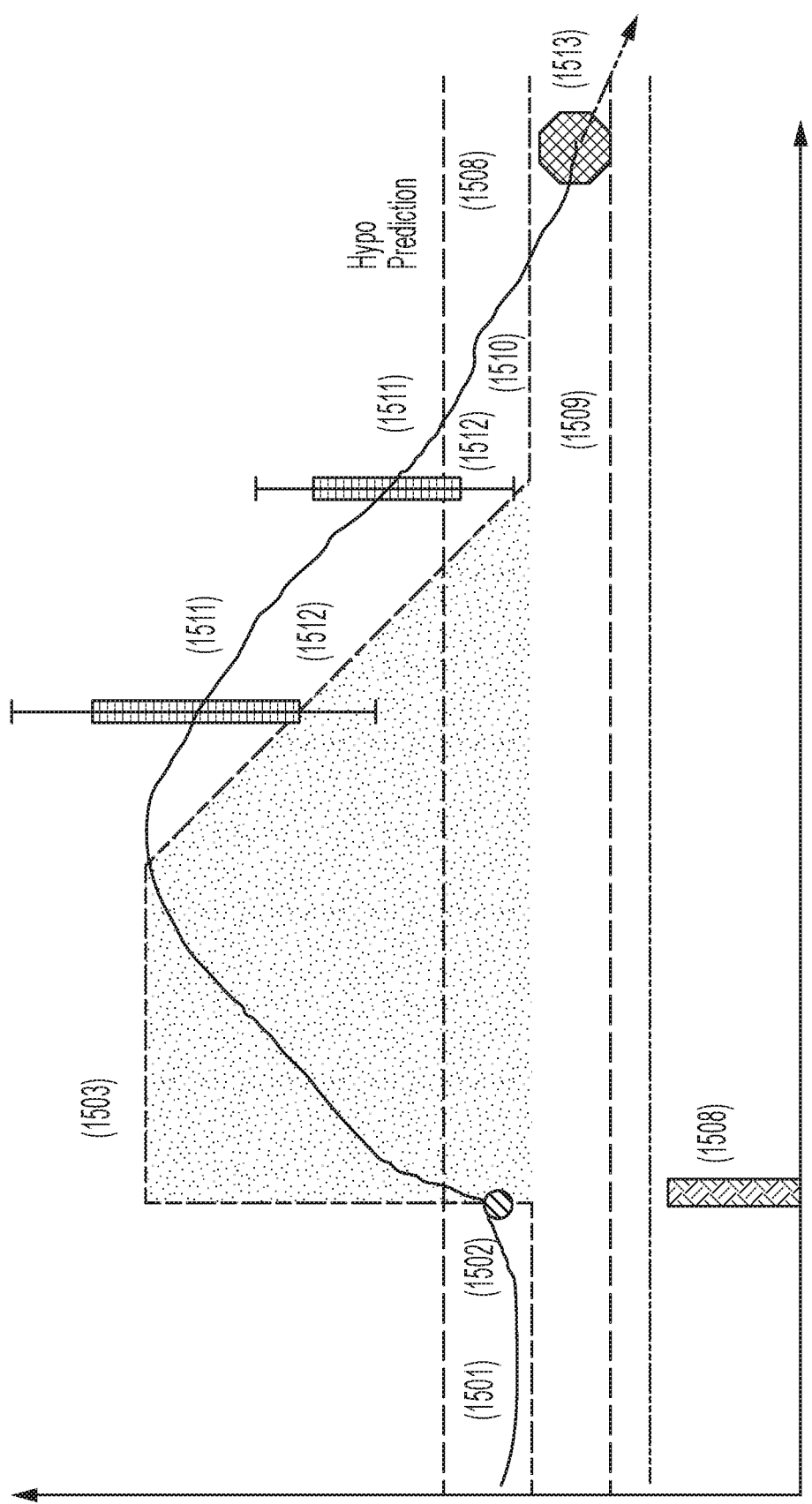

In FIG. 16, the post-prandial CGM data does not result in an alert because the probability of administering a correction bolus if an SMBG measurement was made never exceeds the necessary threshold. In both FIGS. 15 and 16, the system would not alert because the probability of needing a correction bolus of at least $I_0$ does not exceed the required threshold.

Figure 17:
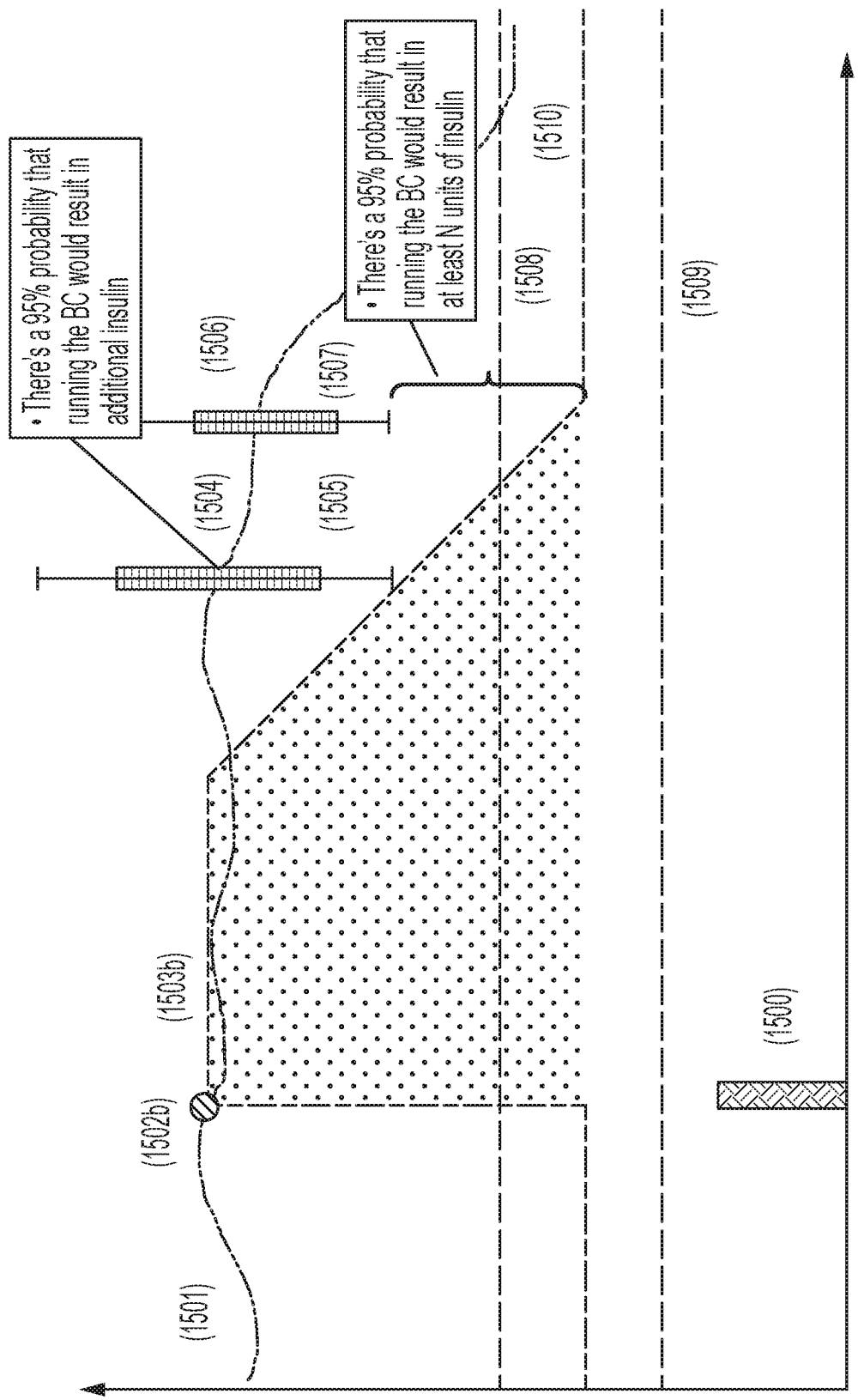

In FIG. 17, an alert results after a correction bolus. Specifically, the example in FIG. 17 is the same as in FIG. 15 except that the trapezoid is the result of a correction dose instead of a meal.

Figure 18:
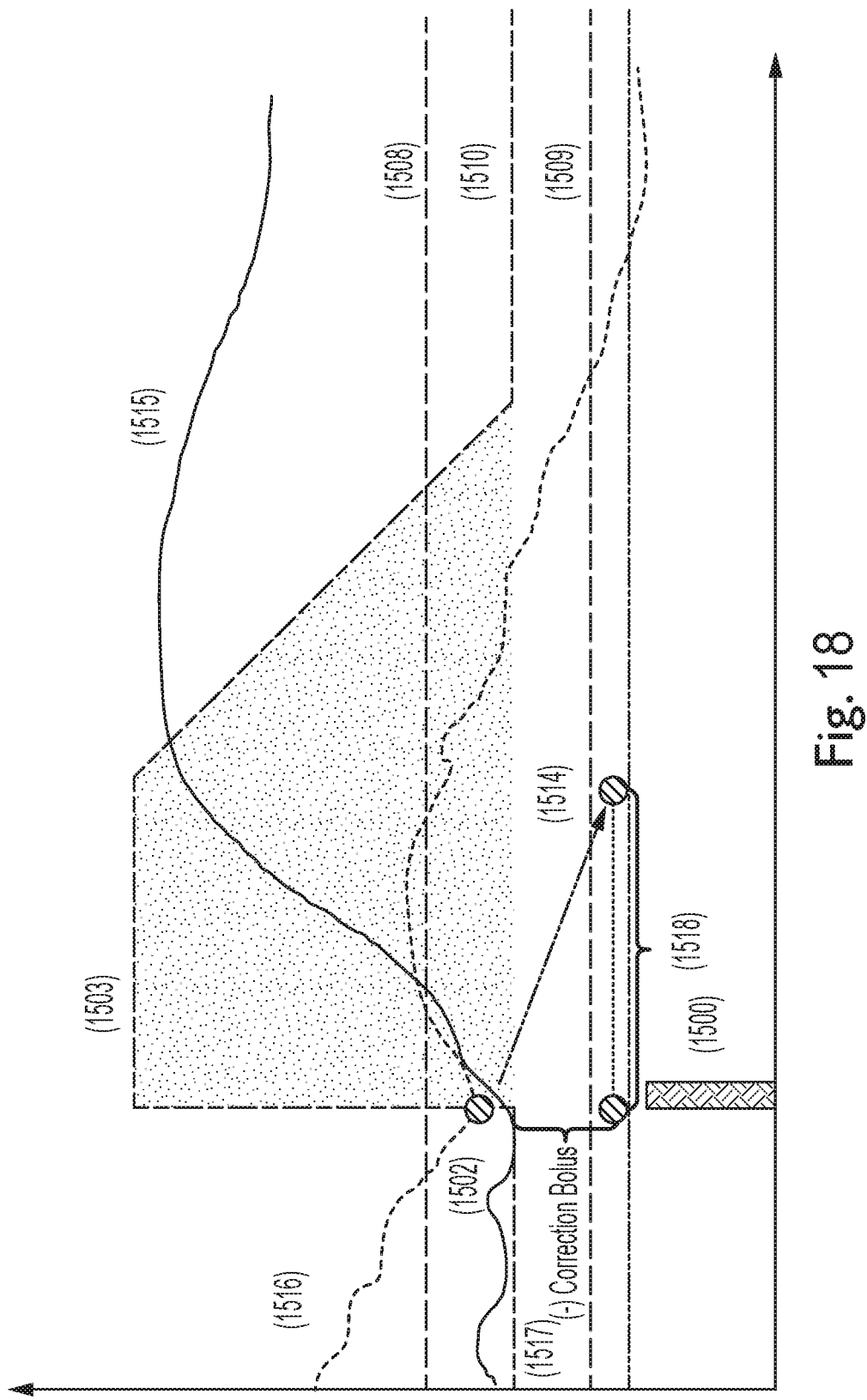

In FIG. 18, a safety reduction is included in a meal bolus when the rate-of-change is negative.

Figure 19:
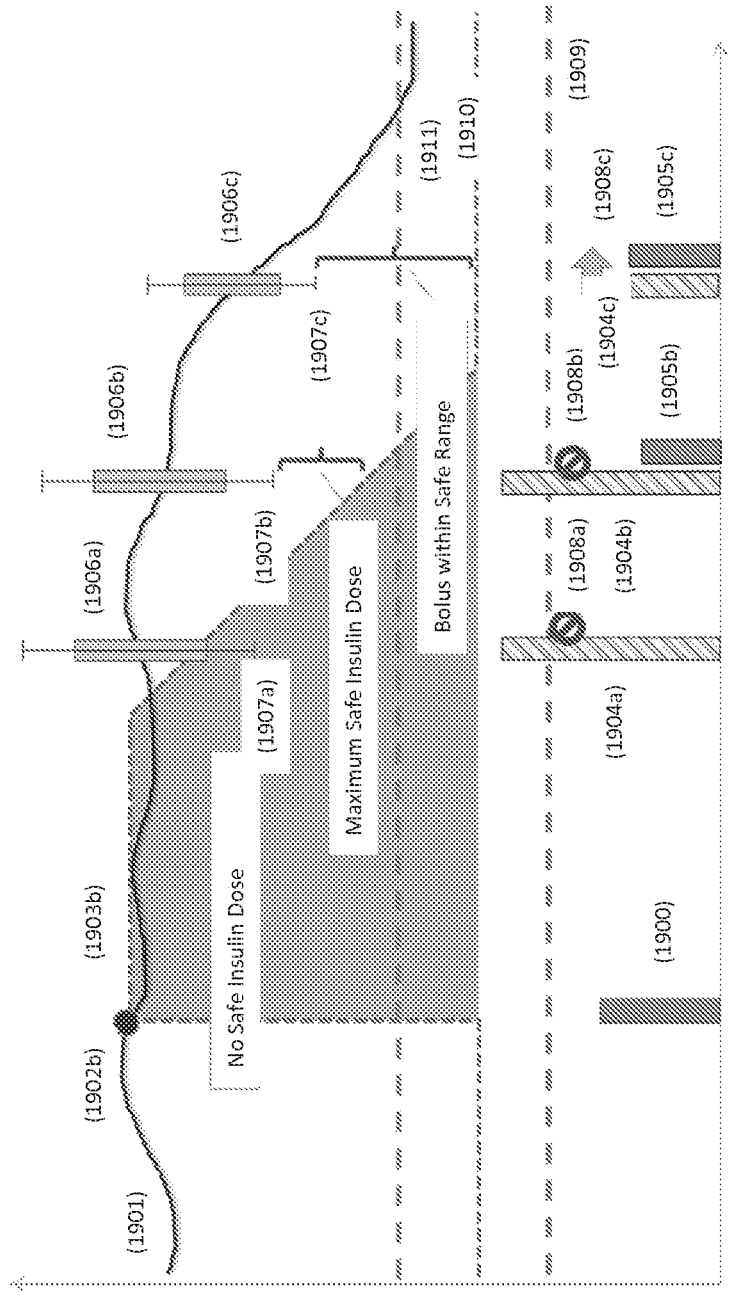
FIG. 19 shows an example of CGM data and the resulting response of at least one embodiment of methods of the present disclosure.

In FIG. 19, three scenarios for the insulin stacking alarm are shown. Below are the descriptions for the labels found in FIG. 19:

1900—Bolus calculated by the bolus calculator based on SMBG (1902*b*)
1901—CGM trace
1902*b*—SMBG measurement used by the bolus calculator
1903*b*—Maximum allowable blood glucose determined by the bolus calculator
1904*a*—Request for a manual bolus for scenario A
1906*a*—CGM value for scenario A
1907*a*—Value for $g_p$ for scenario A
1908*a*—Alarm is given for scenario A because the value for $I_S$ would be negative since $g_p < g_m$. So without an SMBG measurement or associated carbs, this bolus request would likely result in insulin stacking.
1904*b*—Request for a manual bolus for scenario B

1905b—Maximum safe bolus, $I_S$, and the bolus value selected for scenario B
1906b—CGM value for scenario B
1907b—Value for $g_\rho$ for scenario B
1908b—Alarm is given for scenario B because the value for $I_S$ is less than the value for I. In this case the PwD selects the option to reduce the bolus amount to the maximum safe bolus (1905b)
1904c—Request for a manual bolus for scenario C
1905c—Requested bolus if given since it is less than the Maximum safe bolus, $I_S$ for scenario C
1906c—CGM value for scenario C
1907c—Value for $g_\rho$ for scenario C
1908c—There is no alarm for scenario C because the requested bolus amount is less than the maximum safe bolus.
1909—Lower target range
1910—Target value
1911—Upper target range The use of at least one embodiment of the algorithm to address insulin stacking may involve a few separate examples.

Example 1

Manual bolus entered on pump while the controller is present and in communication with the pump. The pump sends the bolus request to the controller. The controller calculates if an alarm should be sent. The controller sends the alarm state back to the pump. If an alarm is necessary, the pump alerts the PwD and provides a set of options.

Example 2

Manual bolus entered on pump while the controller is not present or is not in communication with the pump. The pump cannot communicate directly with the CGM. In such an example, the system cannot implement this algorithm.
Option 1: Accept all manual boluses.
Option 2: Suggest that the PwD should run the Bolus Calculator and then accept the manual bolus.

Example 3

Manual bolus entered on pump while the controller is not present or is not in communication with the pump. The pump can communicate directly with the CGM. The pump requests the most recent CGM value and uncertainty. The pump calculates the maximum safe bolus based on the bolus history and CGM data. If an alarm is necessary, the pump alerts the PwD and provides a set of options.

It should now be understood that the methods and systems described herein may be used to estimate the glucose level of a person having diabetes and to alert the person with diabetes upon reaching a defined probability that an insulin dose is needed. The methods described herein may be stored on a computer-readable medium which has computer-executable instructions for performing the methods. Such computer-readable media may include compact discs, hard drives, thumb drives, random-access memory, dynamic random-access memory, flash memory, and so forth.

It is noted that recitations herein of a component of the present disclosure being "configured" in a particular way, "configured" to embody a particular property, or function in a particular manner, are structural recitations, as opposed to recitations of intended use. More specifically, the references herein to the manner in which a component is "configured" denotes an existing physical condition of the component and, as such, is to be taken as a definite recitation of the structural characteristics of the component.

While particular embodiments and aspects of the present invention have been illustrated and described herein, various other changes and modifications may be made without departing from the spirit and scope of the invention. Moreover, although various inventive aspects have been described herein, such aspects need not be utilized in combination. It is therefore intended that the appended claims cover all such changes and modifications that are within the scope of this invention.

The invention claimed is:

1. A method of administering a safety insulin bolus for alerting a person having diabetes, the method comprising:
receiving into a computing device a plurality of measured glucose values from a continuous glucose monitoring system with a glucose sensor coupled to a person having diabetes;
calculating with the computing device a glucose threshold ($g_{I_o}$) based upon a maximum allowable glucose, a correction factor, and a minimum insulin dose;
calculating with the computing device variance of the plurality of measured glucose values;
calculating by the computing device a boundary glucose value ($g_p$) based upon a probability threshold where the person having diabetes requires at least a predetermined insulin dose, a glucose value from the plurality of measured glucose values, and the variance calculated;
executing, by the computing device, an alert via a user interface, wherein the alert indicates that a glucose measurement should be taken and the alert is executed when the computing device compares the boundary glucose value ($g_p$) to the glucose threshold ($g_{I_o}$) and determines that the boundary glucose value ($g_p$) is greater than the glucose threshold ($g_{I_o}$), and
administering a safety insulin bolus to the person having diabetes upon executing the alert that a glucose measurement should be taken and the computing device determining that the glucose measurement has not been performed and a correction dose has not been administered, wherein the safety insulin bolus is determined by the computing device using the boundary glucose value.

2. The method of claim 1, further comprising determining a maximum safe insulin bonus.

3. The method of claim 2, further comprising producing an alarm on the user interface if a manual bolus request exceeds the maximum safe insulin bolus.

4. The method of claim 1, wherein calculating the boundary glucose value ($g_\rho$) is according to:

$$g_\rho = \sqrt{2\sigma_g^2} \, erf^{-1}(2\rho-1) + g,$$

wherein
$\sigma_g^2$ is a variance of glucose measurement,
$\rho$ is the probability threshold that the person having diabetes requires at least a predetermined insulin dose, and
g is a glucose value from the plurality of measured glucose values.

5. The method of claim 1, wherein calculating the glucose threshold ($g_{I_o}$) is according to:

$$g_{I_0} = g_m + cI_0,$$

wherein, g$_m$ is the maximum allowable glucose, c is the correction factor, and I$_0$ is the minimum insulin dose.

6. The method of claim 5, wherein at least one of the maximum allowable glucose, the minimum insulin dose, and the correction factor are supplied by a bolus calculator.

7. The method of claim 1, wherein the predetermined insulin dose is 1 unit.

8. The method of claim 1, wherein the glucose threshold is dependent on the time of day.

9. The method of claim 1, wherein the probability threshold is selected from a group consisting of 99%, 98%, 90%, 75%, and 50%.

10. The method of claim 1, wherein a day is broken into a plurality of time blocks, at least one of the plurality of time blocks having a different glucose threshold than the remaining time blocks.

11. The method of claim 1, wherein the predetermined insulin dose is higher during a period of sleep than a waking period.

12. The method of claim 1, wherein the plurality of measured glucose values comprise periodic glucose measurements taken approximately every one minute.

13. The method of claim 1, wherein the alert may be a display, sound, vibration, or any combination thereof.

14. The method of claim 1 wherein the glucose measurement is a self-monitored blood glucose measurement.

15. The method of claim 1, wherein the glucose measurement is an additional measurement taken by the continuous glucose monitoring system and triggered by a user.

16. The method of claim 1, further comprising determining an insulin bolus dose with the computing device using a glucose measurement.

17. The method of claim 16, wherein the determining of the insulin bolus dose uses at least one of a rate of change measurement of the plurality of measured glucose values, a trend in the plurality of measured glucose values, and a pattern in the plurality of measured glucose values.

18. The method of claim 16, wherein the determining of the insulin bolus dose uses at least one rate of change measurement of the plurality of measured glucose values, and a predicted glucose value, wherein the correction dose is $$I_c = \frac{1}{c}(g + \dot{g}\tau - g_t);$$

wherein c is a correction factor, g is a glucose value from the plurality of measured glucose values, $\dot{g}$ is a glucose rate-of-change, $\tau$ is a predicted time, and g$_t$ is a predicted glucose level at time t.

19. The method of claim 18, wherein time t is about 20 minutes to about 60 minutes.

20. The method of claim 1, further comprising determining by the computing device normal functioning of the glucose sensor of the continuous glucose monitoring system by using a probability analysis tool configured to calculate a probability of glucose sensor accuracy (PA) based on changes in the received measured glucose values, and said method further comprises weighting the received measured glucose values with the calculated probability of glucose sensor accuracy (PA), and calculating an estimated glucose level of the person by using the weighted received measured glucose values in a recursive filter which minimizes at least effect of a malfunction in the glucose sensor, wherein the probability analysis tool is selected from a state machine and a hidden Markov model, and the recursive filter is selected from a Kalman filter and an Extended Kalman filter.

21. A system for administering a safety insulin bolus to a person having diabetes upon a probability of needing insulin exceeding a threshold level, the system comprising:

a controller, a user interface, and a computer readable medium having computer executable instructions which upon execution by the controller causes the controller to:

receive a plurality of measured glucose values from a glucose sensor coupled to a person having diabetes, calculate a glucose threshold (g$_{I_o}$) based upon a maximum allowable glucose, a correction factor, and a minimum insulin dose, calculate variance of the plurality of measured glucose values, calculate a boundary glucose value (g$_\rho$) based upon a probability threshold where the person having diabetes requires at least a predetermined insulin dose, a glucose value from the plurality of measured glucose values, and the variance calculated, execute an alert, via the user interface, wherein the alert indicates that a glucose measurement should be taken and the alert is executed when the controller compares the boundary glucose value (g$_\rho$) to the glucose threshold (g$_{I_o}$) and determines that the boundary glucose value (g$_\rho$) is greater than the glucose threshold (g$_{I_o}$), and administer a safety insulin bolus to the person having diabetes upon executing the alert that a glucose measurement should be taken and determine the glucose measurement has not been performed and a correction dose has not been administered, wherein the safety insulin bolus is determined by use of the boundary glucose value; and a bolus calculator in communication with the controller, wherein the bolus calculator is configured to determine an insulin bolus based on the plurality of measured glucose values.

22. The system of claim 21, wherein the controller is configured to calculate a maximum safe insulin bolus.

23. The system of claim 21, wherein the controller is configured to produce an alarm on the user interface if a manual bolus request entered in the user interface exceeds the maximum safe insulin bolus.

24. The system of claim 21, wherein the computer executable instructions further cause the controller to determine a glucose rate of change of the plurality of measured glucose values, wherein the glucose rate of change is used by the bolus calculator to modify the insulin bolus.

25. The system of claim 24, wherein the controller displays on the user interface the modified insulin bolus.

26. The system of claim 24, wherein the computer executable instructions further cause the controller to utilize the rate of change to predict a glucose level at a future time for use by the bolus calculator.

27. The system of claim 21, wherein the computer executable instructions further cause the controller to: calculate a probability of glucose sensor accuracy (PA) based on changes in the received measured glucose values using a probability analysis tool, weight the received measured glucose values with the calculated probability of glucose sensor accuracy (PA), and calculate an estimated glucose level of the person by use of the weighted received measured glucose values in a recursive filter which minimizes at least effect of a malfunction in the glucose sensor, wherein the probability analysis tool is selected from a state machine and a hidden Markov model, and the recursive filter is selected from a Kalman filter and an Extended Kalman filter.

28. The system of claim 21, wherein:
the boundary glucose value ($g_\rho$) is calculated according to:

$$g_\rho = \sqrt{2\sigma_g^2} \, erf^{-1}(2\rho-1) + g,$$

wherein
   $\sigma_g^2$ is a variance of glucose measurement,
   $\rho$ is the probability threshold that the person having diabetes requires at least a predetermined insulin dose, and
   g is a glucose result from the plurality of measured glucose values, the glucose threshold ($g_{I_0}$) is calculated according to:

$$g_{I_0} = g_m + cI_0,$$

wherein,
   $g_m$ is the maximum allowable glucose,
   c is the correction factor, and
   $I_0$ is the minimum insulin dose;
the probability threshold is selected from a group consisting of 99%, 98%, 90%, 75%, and 50%; and
at least one of the maximum allowable glucose, the minimum insulin dose, and the correction factor are supplied by the bolus calculator.

* * * * *